US 011419600B2

(12) United States Patent
Binmoeller et al.

(10) Patent No.: US 11,419,600 B2
(45) Date of Patent: Aug. 23, 2022

(54) HANDLE MECHANISM, DELIVERY SYSTEM AND OPERATION METHOD

(71) Applicants: Micro-Tech (Nanjing) Co., Ltd., Jiangsu (CN); Kenneth F. Binmoeller, Rancho Santa Fe, CA (US)

(72) Inventors: Kenneth F. Binmoeller, Rancho Santa Fe, CA (US); Matthew Thomas Yurek, San Diego, CA (US); Michael Hartsfield, Poway, CA (US); John Greelis, Carlsbad, CA (US); Jin Hongyan, Jiangsu (CN)

(73) Assignees: MICRO-TECH (NANJING) CO., LTD., Nanjing (CN); Kenneth F. Binmoller, Rancho Santa Fe, CA (US)

( * ) Notice: Subject to any disclaimer, the term of this patent is extended or adjusted under 35 U.S.C. 154(b) by 135 days.

(21) Appl. No.: 17/063,902

(22) Filed: Oct. 6, 2020

(65) Prior Publication Data

US 2021/0298739 A1    Sep. 30, 2021

Related U.S. Application Data

(63) Continuation-in-part of application No. 16/832,131, filed on Mar. 27, 2020.

(51) Int. Cl.
*A61B 17/04* (2006.01)
*A61B 17/00* (2006.01)

(52) U.S. Cl.
CPC ...... *A61B 17/0401* (2013.01); *A61B 17/0467* (2013.01); *A61B 17/0469* (2013.01); *A61B 2017/00296* (2013.01); *A61B 2017/00389* (2013.01); *A61B 2017/0409* (2013.01)

(58) Field of Classification Search
CPC ............ A61B 17/0401; A61B 17/0467; A61B 17/0469; A61B 17/0487; A61B 2017/00004; A61B 2017/00296; A61B 2017/0034; A61B 2017/00389; A61B 2017/00407; A61B 2017/00818; A61B 2017/0409; A61B 2017/0441; A61B 2017/0464; A61B 2017/0488; A61B 2017/0496

See application file for complete search history.

(56) References Cited

U.S. PATENT DOCUMENTS

2012/0283757 A1*  11/2012  Miller ................ A61F 2/2445
                                                    606/151

* cited by examiner

*Primary Examiner* — Mohamed G Gabr
(74) *Attorney, Agent, or Firm* — Mai-Tram D. Lauer; Westman, Champlin & Koehler, P.A.

(57) ABSTRACT

Disclosed is a handle mechanism, including: a body, a first anchor delivery device provided to the body, a second anchor delivery device provided to the body, a tightening device provided to the body, and a locking and cutting device provided to the body. The first anchor delivery device is configured to control a first tissue anchor. The second anchor delivery device is configured to control a second tissue anchor. The tightening device is configured to pull a suture member.

21 Claims, 13 Drawing Sheets

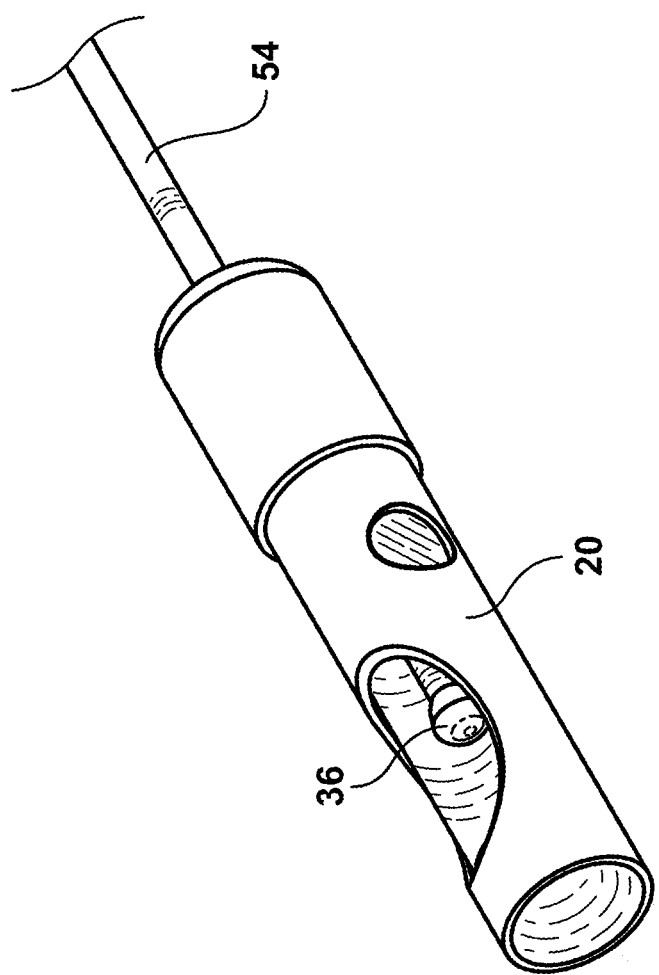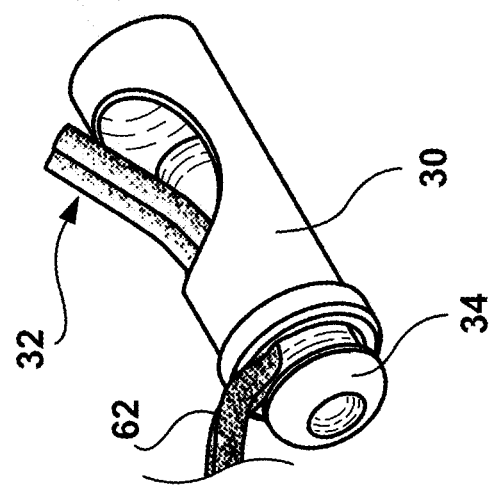
FIG. 6

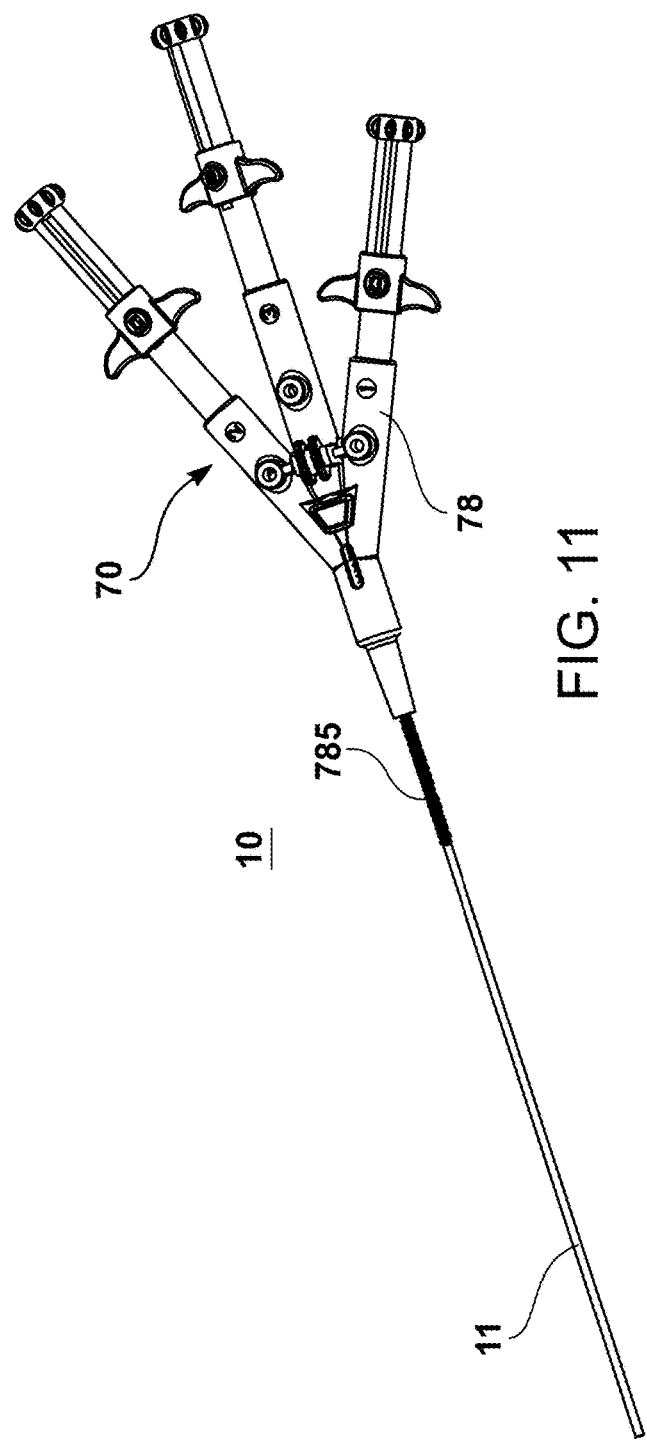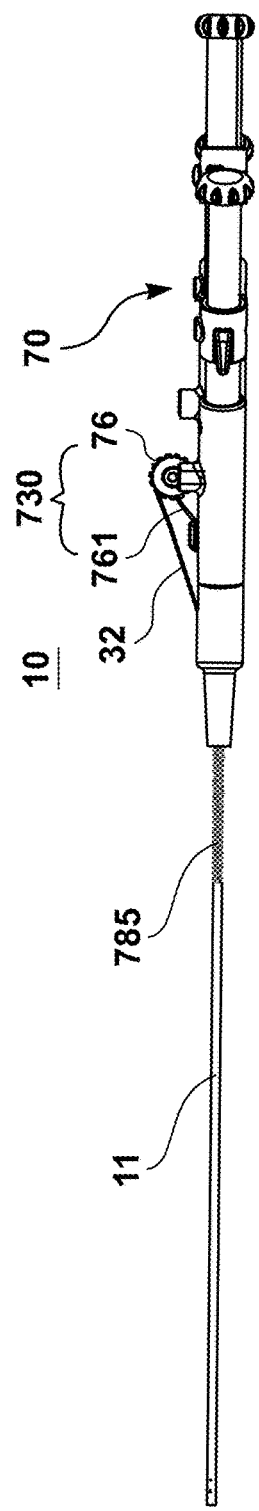

HANDLE MECHANISM, DELIVERY SYSTEM AND OPERATION METHOD

CROSS-REFERENCE TO RELATED APPLICATIONS

This application is a continuation-in-part application of U.S. patent application Ser. No. 16/832,131 filed on Mar. 27, 2020, this U.S. Patent Application is a divisional application of U.S. patent application Ser. No. 15/661,613 filed on Jul. 27, 2017, which claims priority to U.S. Provisional Patent Application Ser. No. 62/367,592 filed on Jul. 27, 2016, which is incorporated herein by reference in its entirety.

TECHNICAL FIELD

The present disclosure relates to the field of medical devices, and in particular to a handle mechanism, a delivery system, and an operation method.

BACKGROUND ART

During a gastrointestinal endoscopy and treatment procedure, the operator often desires to repair or reconstruct a tear or defect, or otherwise approximate or fix tissue or other material by suturing.

Metallic clipping devices were first introduced for the primary purpose of achieving hemostasis of focal gastrointestinal bleeding. Indications for their use have expanded to include closure of perforations and fistulas, securing of catheters and stents, and being a marking device to direct endoscopic, surgical, and radiological therapy, among others. Several endoscopic clipping devices are commercially available, which all consist of metallic double or triple prongs (forks) joined at the proximal end. The prongs of the clip are applied with pressure onto the target tissue and clamped and closed by manually squeezing the catheter handle assembly. Clipping devices are limited by a fixed distance and relationship between the prongs.

The fixed distance between the prongs limits the operator's ability to close defects that exceed this distance, which limits applicability to small defects. The fixed relationship between the prongs limits the operator's ability to position the clip appropriately in relation to the area in need of treatment. For instance, the clip may not be able to close a defect that is approached tangentially at a curve or angle. Further, because the proximal ends of the legs are joined, the operator may not be able to adjust the positioning of prong of one clip without affecting the positioning of the prong of the second clip. Positioning also may be limited because the clip may not be properly oriented when it is deployed or the clip may slip out of alignment during application. Finally, the legs of presently used clip must be actuated and anchored at the same time. If unequal pressure is applied to the legs during anchoring, closure may be sub-therapeutic and scissoring of the legs may occur that can result in tissue damage. Presently used clips are only capable of capturing the mucosa and do not penetrate into the deeper wall layers (submucosa and muscular propria layers).

A suturing device that addresses the limitations of clips is the Apollo Overstitch. This device provides a curved needle movable on an arm to pierce tissue and perform tissue approximation and suturing. This device is capable of full-thickness (entire bowel wall) tissue capture and the closure of larger defects, however, the device cannot be delivered through the working (operative) channel of the endoscope and must be pre-mounted on the end of the endoscope. It also involves multiple time consuming, technically demanding maneuvers and manipulations. A need remains for an endoscopic tissue closure device, which addresses the limitations of presently used clips and is capable of full-thickness tissue capture.

The Ovesco "over-the-scope-clip" (OTSC) can achieve full-thickness closure of a defect by suctioning tissue into a cap attachment mounted on the end of the endoscope. The clip, mounted on the cap attachment, is released by turning a hand wheel, similar to band ligation. The size of the defect that can be closed is small, which limited by the diameter of the cap attachment. Like the Apollo Overstitch, the OTSC must be pre-mounted onto the endoscope prior to use.

Accordingly, it would be desirable to obtain a multiple tissue anchor and delivery system for facilitating the repair of wall defects, plication of tissue, and treatment of lesions delivered through the working channel of the endoscope.

It would also be desirable to obtain a multiple tissue anchor and delivery system for repairing wall defects, achieving plication of tissue, and treating lesions, whereby the apparatus and method have the capability to facilitate repair of defects of any size, plicate tissues of any size, and treatment of lesions of any size, with deployment of each anchor independent of one another under direct endoscopic visualization.

It would also be desirable to obtain a multiple tissue anchor and delivery system, so as to provide treatment of relatively large perforations, lesions and damage areas under endoscopic visualization.

It would also be desirable to obtain a handle mechanism, a delivery system, and an operation method for facilitating operation by medical staff, thereby facilitating the repair of wall defects, plication of tissue, and treatment of lesions delivered through the working channel of the endoscope.

SUMMARY

An embodiment of the present disclosure provides a handle mechanism, comprising:
a body;
a first anchor delivery device provided to the body, wherein the first anchor delivery device is configured to control a first tissue anchor, so that the first tissue anchor is anchored into a tissue and released;
a second anchor delivery device provided to the body, wherein the second anchor delivery device is configured to control a second tissue anchor, so that the second tissue anchor is anchored into a tissue and released;
a cinching device (tightening device) provided to the body, wherein the tightening device is configured to pull a suture member to cinch (tighten) the first tissue anchor and the second tissue anchor connected to the suture member; and
a locking and cutting device provided to the body, wherein the locking and cutting device is configured to lock the suture member to an inner tubular member, cut the suture member, and completely release the inner tubular member and a portion of the suture member connected to the inner tubular member.

An embodiment of the present disclosure further provides a delivery system, comprising the handle mechanism described above.

An embodiment of the present disclosure further provides an operation method, which is implemented using the handle mechanism described above, comprising:
accessing and visualizing a treatment area using an endoscope;

delivering the distal ends of the first tissue anchor, the second tissue anchor, the inner tubular member, and the suture member to a distal end of the endoscope through a working channel of the endoscope;

operating the first anchor delivery device to anchor the first tissue anchor into a first target tissue and release the first tissue anchor;

operating the second anchor delivery device to anchor the second tissue anchor into a second target tissue and release the second tissue anchor;

operating the tightening device to pull the suture member and tighten the first tissue anchor and the second tissue anchor connected to the suture member, so as to tighten the first target tissue and the second target tissue; and operating the locking and cutting device to lock the suture member to the inner tubular member, cut the suture member, and completely release the inner tubular member and a portion of the suture member connected to the inner tubular member.

BRIEF DESCRIPTION OF DRAWINGS

FIG. 6 is a perspective view of the suture tightening and excising inner tubular member and the third intermediary inner tubular member, whereby the distal and proximal sections have been separated from each other by retraction of the distal cap ball mechanism and wherein retraction of the proximal section cuts the suture or strap.

FIG. 11 shows a schematic view, from a first perspective, of another delivery system according to an embodiment of the present disclosure.

FIG. 12 shows a schematic view, from a second perspective, of another delivery system according to an embodiment of the present disclosure.

Corresponding reference signs indicate corresponding parts throughout the several figures. The exemplifications set out herein illustrate exemplary embodiments of the present disclosure, and such exemplifications are not to be construed as limiting the scope of the present disclosure in any manner.

DETAILED DESCRIPTION OF EMBODIMENTS

Figure 1:
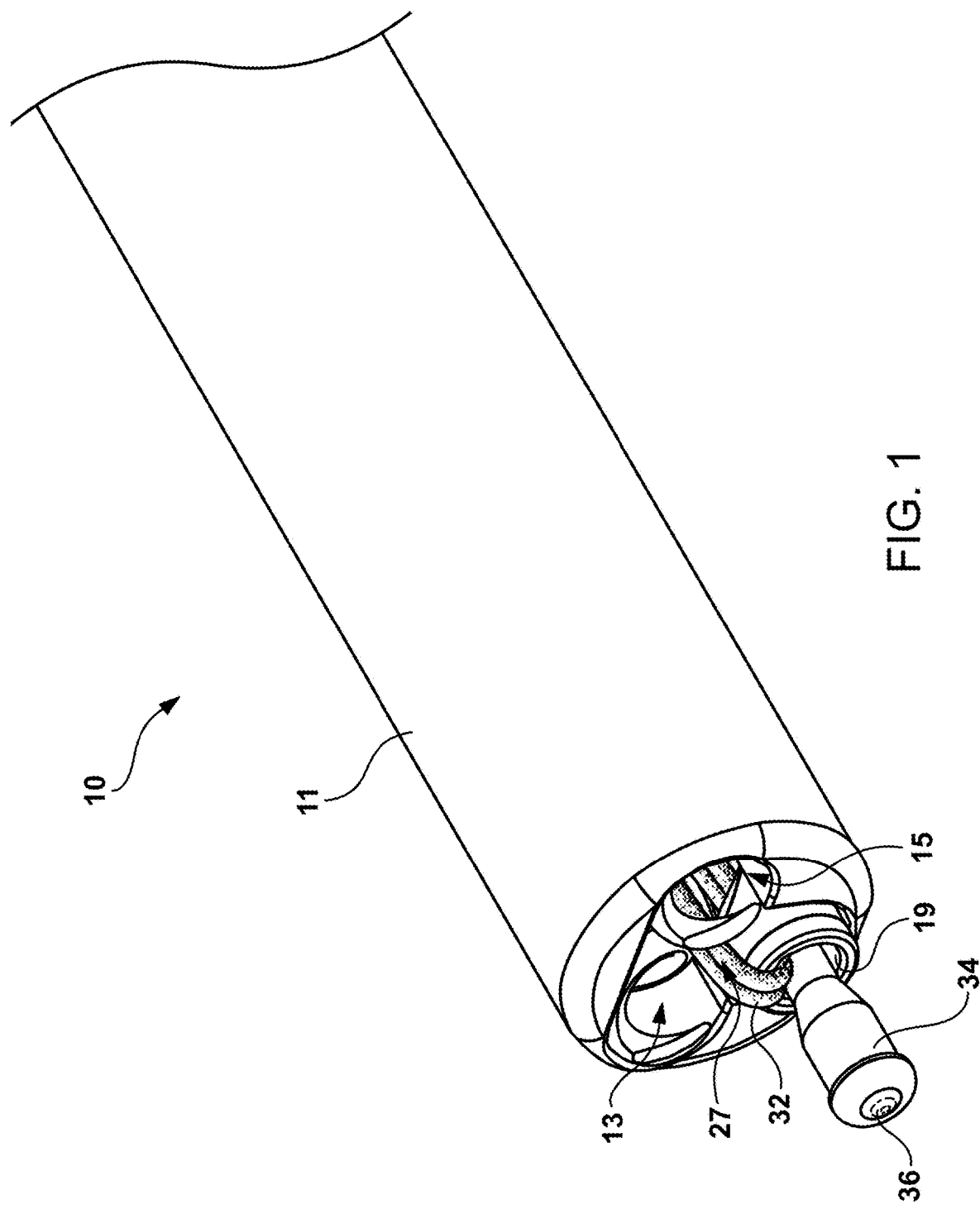
FIG. 1 is a perspective view of the distal end of the catheter system showing the multi-lumen catheter showing the first and second inner tubular members which correspond to the first and second helical anchors and a third inner tubular member showing the tightening device and a fourth inner tubular member with the suture strap mechanism engaged to the proximal end of an elongated shaft.

The present disclosure comprises a novel delivery system for delivering two or more helical anchors through an endoscope or colonoscope to repair a wall defect, achieve plication of tissue, or treat a lesion. The delivery system comprises an outer sheath tubular member designed to pass through the working channel of an endoscope.

Axially in parallel contained within the outer sheath tubular member are three individual inner tubular members, a first inner tubular member being designed to deploy a first helical tissue anchor (sometimes referred to as the "first helical device" hereinafter), a second inner tubular member being designed to deploy a second helical tissue anchor (sometimes referred to as the "second helical device" hereinafter), and a third inner tubular member containing a retraction member. The first inner tubular member coaxially contains a first reinforced tubular member that has a control wire allowing rotational manipulation of the first helical tissue anchor designed to be embedded into the wall tissue. The first inner tubular member also has a lumen, whereby a first control wire is coaxially enclosed therein to release the first helical anchor. After the first helical tissue anchor is embedded into the wall tissue, it is released and the first inner tubular member is retracted proximally. The second inner tubular member coaxially contains a second reinforced tubular member that has a control wire allowing rotational manipulation of the second helical tissue anchor to be embedded into the wall tissue. The second inner tubular member also has a lumen, whereby a second control wire is coaxially enclosed therein to release the second helical tissue anchor. After the second helical tissue anchor is embedded into the wall tissue, it is released and the second inner tubular member is retracted proximally. Attached to the first helical tissue anchor and to the second helical tissue anchor is a strap or suture member that is contained within the third inner tubular member.

The strap or suture member is engaged to the third inner tubular member that when moved distally causes the suture member to become tightened between the first and second helical tissue anchors, compelling the two helical tissue anchors together and partially or fully closing the treatment area.

A novel handle assembly can be attached to the proximal end of the outer sheath tubular member which surrounds the first inner tubular member, the second inner tubular member, and the third inner tubular member. The handle assembly includes a plurality of rotating thumbwheels, slide buttons and release mechanisms.

In clinical operation, the access to and visualization of the treatment area is first conducted using standard endoscopy techniques. The clinician passes the delivery system through the working channel of the endoscope.

To engage one side of the lesion area, the clinician advances one of the thumb slides forward, advancing the first tissue helical anchor and its delivery catheter out of the distal end of the outer catheter sheath. The first helical device and its delivery catheter can be visualized endoscopically. The clinician manipulates the endoscope and maneuvers the first helical tissue anchor and its delivery catheter by sliding the ratcheting thumb slide forward, to position the first helical tissue anchor against the target site and then rotates the thumbwheel to embed the first helical device into the mucosal, submucosal or muscle tissue as desired. After the first helical device is satisfactorily embedded into the tissue, the clinician retracts the release mechanism to release the first helical device. This is accomplished by pulling back on the release mechanism behind the ratcheting thumb slide. Once the first helical device is released, pushing the central button on the thumb slide down releases the thumb slide from the ratchet teeth, allowing it to be pulled proximally along with the release mechanism. Retracting the thumb slide back pulls the delivery catheter back into the sheath of the helical device, thereby leaving the first helical device and attached strap or suture in the tissue.

The clinician then engages the other side of the lesion by advancing the other thumb slide forward to advance the second helical tissue anchor and its delivery catheter out of the distal end of the catheter shaft. The second helical tissue anchor and its delivery catheter can be visualized endoscopically. The clinician manipulates the endoscope and maneuvers the second helical device and its delivery catheter, to position the second helical tissue anchor against the target site, and then rotates the thumbwheel to embed the second helical device into the mucosal, submucosal, or muscle layer of the wall as desired. After the second helical device is satisfactorily embedded into the tissue, the clinician retracts back on the release mechanism to release the second helical device. This is accomplished by pulling back on the release mechanism behind the ratcheting thumb slide. Once the second helical device is released, pushing the central button on the second thumb slide down releases the thumb slide from the ratchet teeth, thereby allowing it to be pulled proximally. Retracting the thumb slide back pulls the delivery catheter back into the sheath of the helical device, thereby leaving the second helical device and attached strap or suture in the tissue.

The clinician then advances the third inner tube to pull the two helical devices and their attached tissues together. A ferrell, bolo tie, locking anchor, spring clip or a preformed knot and knot pusher locks the two helical tissue anchors together to partially or fully close the treatment area.

There are two embodiments that perform the same tissue approximation with the anchor and delivery system but differ in the inner delivery catheter mechanisms.

The first embodiment has a single lumen sheath with three elements running throughout its length. Two tubular elements engage the connector, anchor coupler and anchor components. A third tubular element functions to manipulate the strap or suture held by a wire that extends proximally through the handle. After delivery of the anchors, the two tubular elements of the delivery system are retracted out of the sheath and a knot pusher or ferrell is pushed over the third element, and suture or strap tether moves and locks the anchors together, closing the tissue opening.

In the second embodiment, the sheath has a multi-lumen configuration that contains three or four individual lumens that are designed to each contain the three elements and one for the suture or strap. Two lumens of the sheath function to operate the helical devices. The third and fourth lumens contain the suture or strap assembly and a locking mechanism. The third and fourth lumens may be combined, further reducing the catheter's profile. The delivery procedures between the two embodiments are similar, whereby advancement of the third element in the second embodiment is accomplished by advancing the sheath itself. The second embodiment with independent lumens in the sheath for the suture or strap element reduces the potential for twisting around the helical device delivery elements. The third element with its locking mechanism is similar between the two embodiments, whereby they similarly pull on the suture or strap closing the tissue opening. After placement of the catheter tip bringing the tissues together, a handle element is pulled to first pinch and lock the suture or strap element and then to cut it. The delivery system is then removed through the endoscope.

An embodiment of the present disclosure provides a handle mechanism, comprising:

a body;

a first anchor delivery device provided to the body, wherein the first anchor delivery device is configured to control a first tissue anchor, so that the first tissue anchor is anchored into a tissue and released;

a second anchor delivery device provided to the body, wherein the second anchor delivery device is configured to control a second tissue anchor, so that the second tissue anchor is anchored into a tissue and released;

a cinching device (tightening device) provided to the body, wherein the tightening device is configured to pull a suture member to cinch (tighten) the first tissue anchor and the second tissue anchor connected to the suture member; and a locking and cutting device provided to the body, wherein the locking and cutting device is configured to lock the suture member to an inner tubular member, cut the suture member, and completely release the inner tubular member and a portion of the suture member connected to the inner tubular member.

An embodiment of the present disclosure further provides a delivery system, comprising the handle mechanism described above.

An embodiment of the present disclosure further provides an operation method, which is implemented using the handle mechanism described above, comprising:

accessing and visualizing a treatment area using an endoscope;

delivering the distal ends of the first tissue anchor, the second tissue anchor, the inner tubular member, and the suture member to a distal end of the endoscope through a working channel of the endoscope;

operating the first anchor delivery device to anchor the first tissue anchor into a first target tissue and release the first tissue anchor;

operating the second anchor delivery device to anchor the second tissue anchor into a second target tissue and release the second tissue anchor;

operating the tightening device to pull the suture member and tighten the first tissue anchor and the second tissue anchor connected to the suture member, so as to tighten the first target tissue and the second target tissue; and operating the locking and cutting device to lock the suture member to the inner tubular member, cut the suture member, and completely release the inner tubular member and a portion of the suture member connected to the inner tubular member.

Referring now to the drawings and particularly to FIG. 1 which is a perspective view of the present disclosure 10 which includes a distal end of the catheter system showing the multi-lumen catheter 11, a first inner tubular lumen 13 and second inner tubular lumen 15 which correspond to the first and second helical tissue anchors and associated shaft members and third and fourth inner tubular lumens 19 and 27, with the suture strap and tightening mechanism engaged to the proximal end of elongated shaft that travels throughout the length of the multi-lumen catheter and terminates in a connection to the handle mechanism 70.

The multi-lumen catheter can be fabricated from a number of polymeric materials, such as polytetrafluoroethylene (PTFE), FEP, ETFE, polyvinyl chloride (PVC), polyethylene, polypropylene, PEEK, polybutylene, acrylonitrile-butadiene-styrene (ABS), rubber modified styrene, polyacetal, polyethylene, graphite or nylon, or a combination of metal coil or braid encapsulated in the polymeric materials or any combination thereof. The diameter of the first inner tubular lumen 13 and the second inner tubular lumen 15 is in the range of 0.25 mm to 1.2 mm, with a preferred diameter of 0.5 mm. The multi-lumen catheter 11 can have a length in the range of 100 to 500 cm depending on the clinical application.

Figure 2:
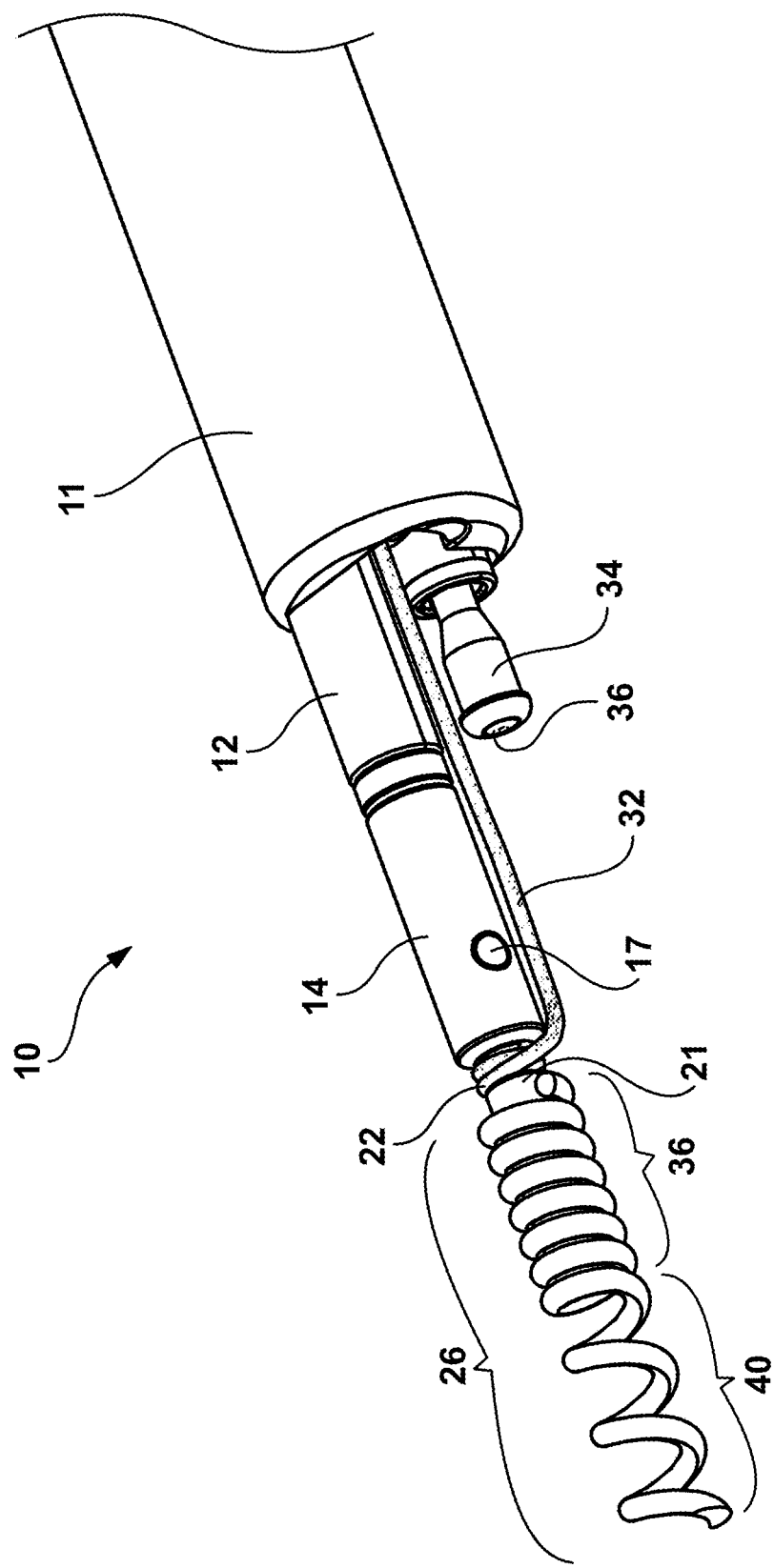
FIG. 2 is a perspective view of the distal end of the helical tissue anchor delivery system showing first helical tissue anchor assembly projecting distally outward from the multi-tubular catheter shaft.
Figure 8:
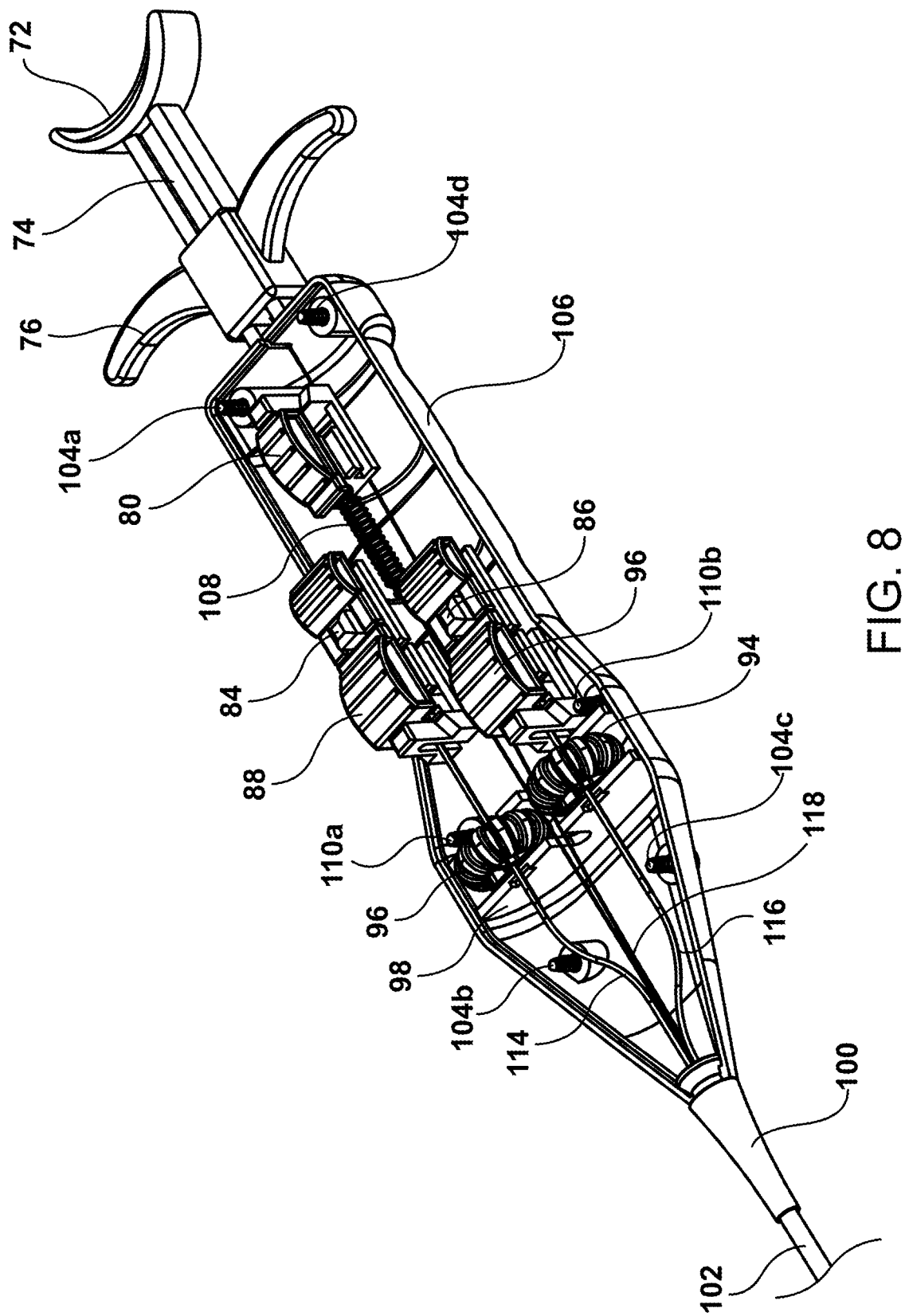
FIG. 8 is a perspective inner view of the proximal handle mechanism with the top body member removed, showing the components and interaction with tubular members.

Now referring to FIGS. 2 and 8, coaxially aligned within the first inner tubular lumen 13 is a first elongated shaft 114 (See FIG. 8) that travels throughout the length of the multi-lumen catheter and terminates in a connection to the handle mechanism 70. The elongated shaft 114 has a series of components that are designed to have a removable component 14 on its distal end. On the distal end of the elongated shaft 114 is a fixed engagement member 12 that coaxially and removably engages a first removable anchor engagement member 14. Not shown is a fork configured mechanism that extends from the distal end of the first engagement member 12 to become coaxially inserted into the first removable anchor coupler member 14. On the surface of each fork configuration member, is a tab that becomes inserted into the hole in the first removable anchor coupler member 14. The first connection tab with corresponding hole/tab assembly 17 is used to removably affix the first engagement member 12 to the first removable anchor coupler member 14.

Attached to the distal end of the first removable anchor engagement member is first helical tissue anchor 26. First helical tissue anchor 26 has two different winds or thread pitches, where the coils are in a tight configuration 36 on the proximal end and have a relatively loose configuration 40 on its distal end. The relatively loose configuration 40 is designed to utilize rotational forces to embed the first helical tissue anchor 26 into the mucosal, submucosal or muscle tissues. It is anticipated by the Applicants that the tight configuration 36 can be appropriately shortened in length to minimize this tight configuration from protruding from the treated tissue area. Also, the depth of tissue anchor capture can be adjusted when embedding the first tissue helical anchor, to enable full-thickness tissue closure and full-thickness plication. Located between the first helical tissue anchor 26 and the first removable anchor engagement member 14 is a suture connection area 21, whereby a suture strap mechanism 22 is affixed by a series of rotations around the suture connected area 21. The suture strap mechanism 22 is designed to allow proximal section of first helical tissue anchor shaft 114, first connector member 12, first removable anchor coupler member 14 and first helical tissue anchor 26 to rotate without the rotation of the suture strap mechanism. The diameter of the first connection member 12 and the first removable anchor coupler member is in the range of 0.25 mm to 1.2 mm, with a preferred diameter of 0.5 mm. First fixed engagement member 12 and first removable anchor engagement member 14 can be fabricated from metallic materials, such as brass, brass alloys, stainless steel, cobalt chrome alloys, nickel titanium, copper alloys, or polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof, or polymeric materials, such as polyvinyl chloride (PVC), polyethylene, polypropylene, PEEK, Ultem, polybutylene, acrylonitrile-butadiene-styrene (ABS), rubber modified styrene, polyacetal, polyethylene, graphite, polyurethane or nylon, or any combination thereof.

The suture strap mechanism 22 can be a mono-strand or multi-strand configuration and can be fabricated from a number of polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof, or polymeric materials, such as polyvinyl chloride (PVC), polyethylene, polypropylene, PEEK, polybutylene, acrylonitrile-butadiene-styrene (ABS), rubber modified styrene, polyacetal, polyethylene, graphite, polyurethane or nylon, or any combination thereof.

Also shown in FIG. 2 is third inner tubular member tightening mechanism 34 and retraction ball mechanism 36 which is engaged to third connection shaft 54.

Figure 3:
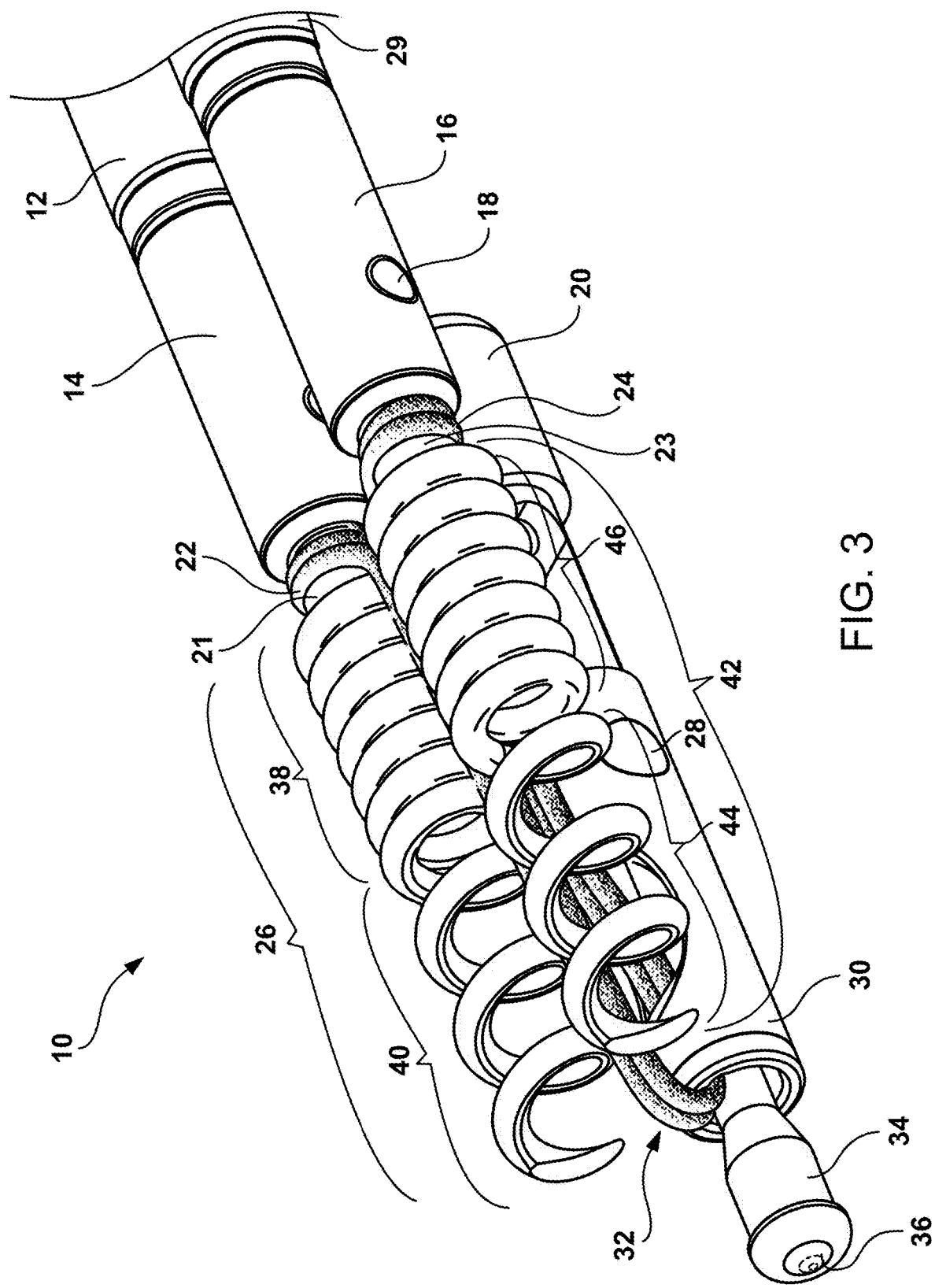
FIG. 3 is perspective inner view of the distal end of the helical tissue anchor delivery system showing the first and second anchor assemblies and the suture cinching (tightening) and excising inner tubular member with the multi-tubular catheter shaft removed.

Now referring to FIGS. 3 and 8, which show an inner perspective view of the distal end of the helical tissue anchor delivery system showing the first and second anchor assemblies and the suture tightening and excising inner tubular member. The first anchor deployment assembly was described the paragraph above, and this paragraph will focus primarily on the second anchor deployment assembly. Coaxially aligned within the second inner tubular lumen 15 is a second elongated shaft 116 that travels throughout the length of the multi-lumen catheter and terminates in a connection to the handle mechanism 70. The second elongated shaft 116 has a series of components that are designed to have a second removable anchor coupler member 16 on its distal end. On the distal end of the elongated shaft 116 is a second fixed engagement member that coaxially and removably engages a second removable anchor engagement member 16. Not shown is a fork configured mechanism that extends from the distal end of the second engagement member 29 to become coaxially inserted into the second removable anchor coupler member 16. On the surface of each fork configuration member, is a tab that becomes inserted into the hole in the second removable anchor coupler member 16. The second connection tab with corresponding hole/tab assembly 18 is used to removably affix the second engagement member 29 to the second removable anchor coupler member 16.

Attached to the distal end of the second removable anchor engagement member is second helical tissue anchor 42. Second helical tissue anchor 42 has two different winds or thread pitches, where the coils are in a tight configuration 46 on the proximal end and have a relatively loose configuration 44 on its distal end. The relatively loose configuration 44 is designed to utilize rotational forces to embed the second helical anchor 42 into the mucosal, submucosal or muscle tissues. It is anticipated by the Applicants that the tight configuration 46 can be appropriately shortened in length to minimize this tight configuration from protruding from the treated tissue area. Also, the depth of tissue capture can be adjusted when embedding the second helical tissue anchor to enable full-thickness tissue closure and full-thickness plication. Located between the second helical tissue anchor 42 and the second removable anchor engagement member 16 is a second suture connection area 23, whereby a suture strap mechanism 22 is affixed by a series of rotations around the second suture connection area 23. The suture strap mechanism 22 is designed to allow proximal section of second tissue anchor shaft 116, second connector member 29, second removable anchor coupler member 16 and second helical tissue anchor 42 to rotate without the rotation of the suture strap mechanism. Second fixed engagement member 29 and second removable anchor engagement member 16 can be fabricated from metallic materials, such as brass, brass alloys, stainless steel, cobalt chrome alloys, nickel titanium, copper alloys, or polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof, or polymeric materials, such as polyvinyl chloride (PVC), polyethylene, polypropylene, PEEK, polybutylene, acrylonitrile-butadiene-styrene (ABS), rubber modified styrene, polyacetal, polyethylene, graphite, polyurethane or nylon, or any combination thereof.

Also shown in FIGS. 3 and 8 are the third suture tightening and excising inner tubular member 30 of the proximally located single suture strap mechanism 118 in an extended configuration, with the third inner tubular tightening mechanism extended out of the distal end of the suture tightening and excising inner tubular member 30 and with retraction ball mechanism 36. The pair of suture strap mechanisms 32 extend out of the third suture tightening and excising inner tubular member 30 and are attached as described above to first and second suture connection areas. The other end of the pair of suture strap mechanisms penetrates a window 50 in the distal end that extends proximally toward the handle and forms a loop at a proximal location (not shown) that engages a proximally located single suture strap mechanism 118 that extends proximally down the catheter lumen to the handle 70. Also shown is an interference catching mechanism 28 that is designed to engage the retraction ball mechanism 36 and retract the suture tightening and excising tubular member 30 proximally back. When the third suture tightening and excising inner tubular member 30 is further retracted proximally, the pair of suture strap mechanisms 32 is cut by the sharp distal end of the window 50 in the third suture tightening and excising inner tubular member 30.

Figure 4:
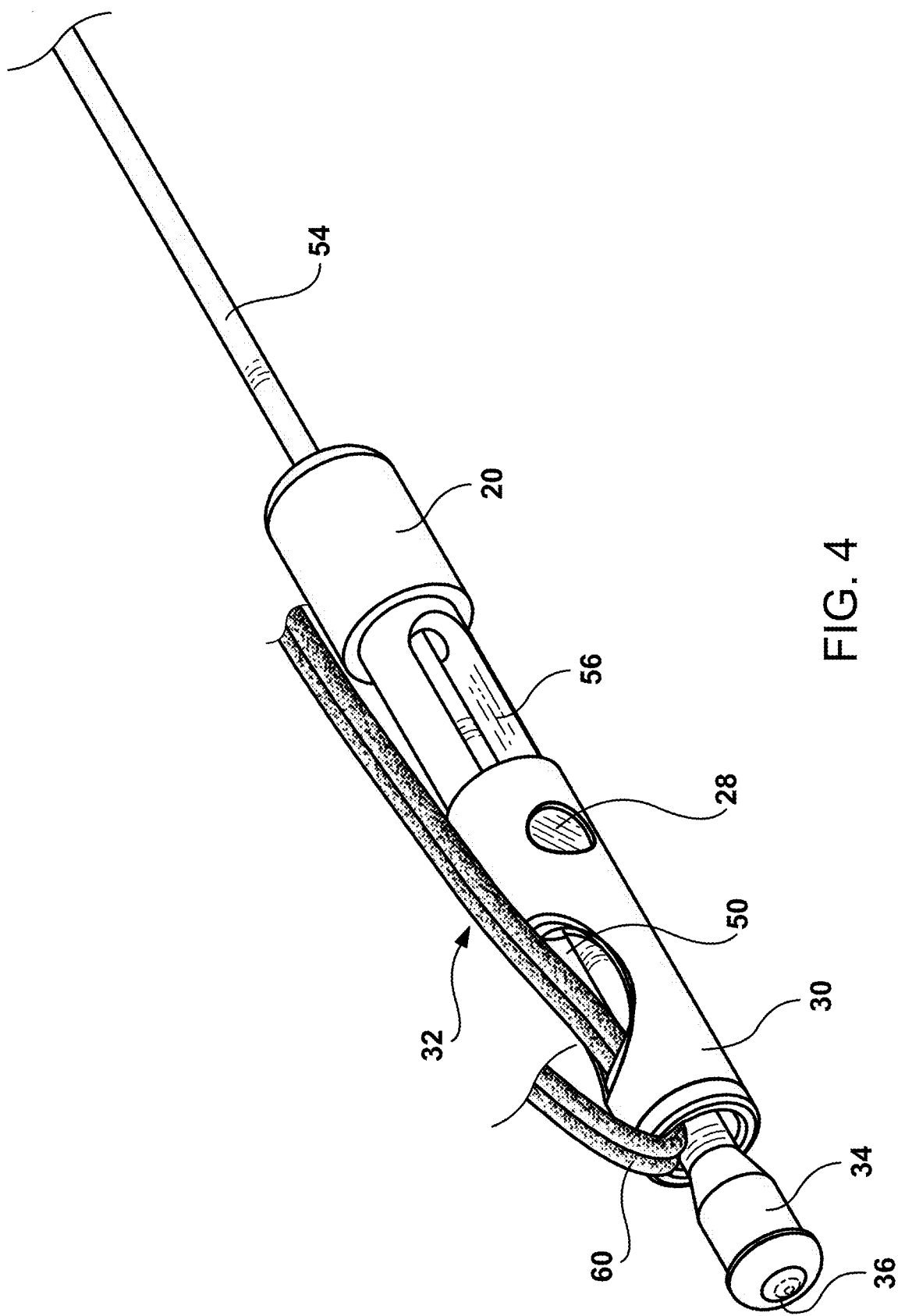
FIG. 4 is a perspective view of the suture tightening and excising inner tubular member having a distal section coaxially engaged to a third intermediary inner tubular member, whereby both are coaxially engaged to an elongated shaft member.

Now referring to FIG. 4 which shows a perspective view of the suture tightening and excising inner tubular member 30 having a distal section coaxially engaged to a proximal third intermediary inner tubular member 20, whereby both are coaxially engaged to the distal section of the elongated shaft member 54. The distal end 54 is connected to the elongated shaft 118 and extends the catheter lumen to the handle assembly 70. On the proximal end is the third intermediary inner tubular member 20 that distally includes a pair of forks 56. The forks are designed to guide interference catching mechanism 28. The window 50 in the third distal inner tubular member 30 is clearly shown with the pair of suture strap mechanisms 32 traveling through the window 50, out the distal end 60, which continues to the first suture strap mechanism connection area 21 and second suture strap mechanism connection area 23.

Figure 5:
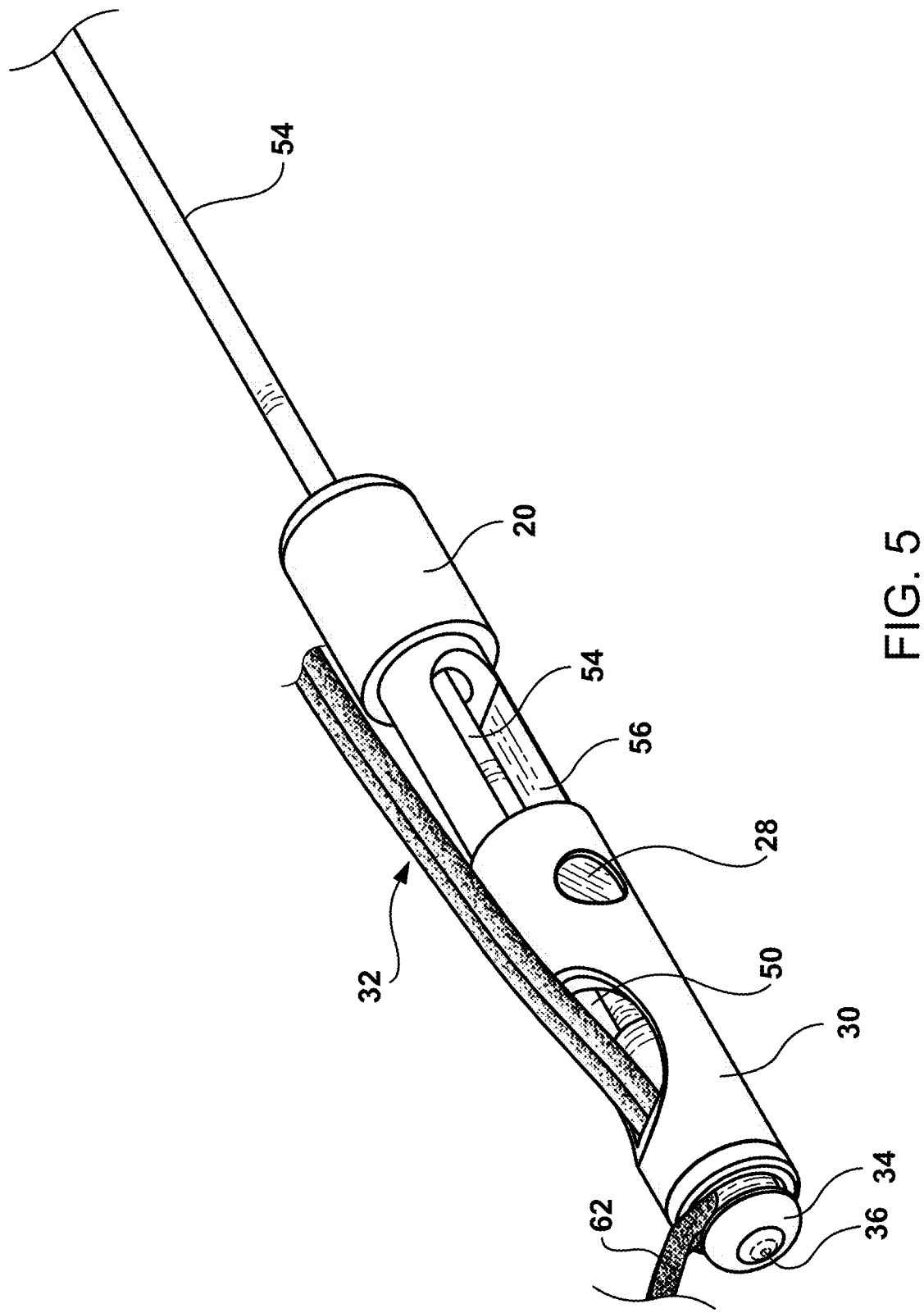
FIG. 5 is a perspective view of the suture tightening and excising inner tubular member and third intermediary inner tubular member, whereby the distal cap is retracted, causing the suture to become tightened between the distal cap and the distal section.

Shown in the perspective view of FIG. 5, is the suture tightening and excising inner tubular member 30 and third intermediary inner tubular member 20, whereby the distal cap 34 is retracted causing the pair of suture strap mechanisms 62 to become tightened between the distal cap 34 and the distal end of the suture tightening and excising inner tubular member 30.

In FIG. 6, shown is a perspective view of the suture tightening and excising inner tubular member 30 and third intermediary inner tubular member 20, whereby the distal and proximal sections have been separated from each other by retraction of the distal cap ball mechanism 36 and wherein retraction of the proximal section cuts the sutures. The incising of the suture strap mechanism generally occurs after the first helical tissue anchor 26 and second helical tissue anchor 42 have been embedded into the mucosal tissue layers and the defect in the wall has been closed by biasing the first helical tissue anchor 26 and second helical tissue anchor 42 toward each other.

Figure 7:
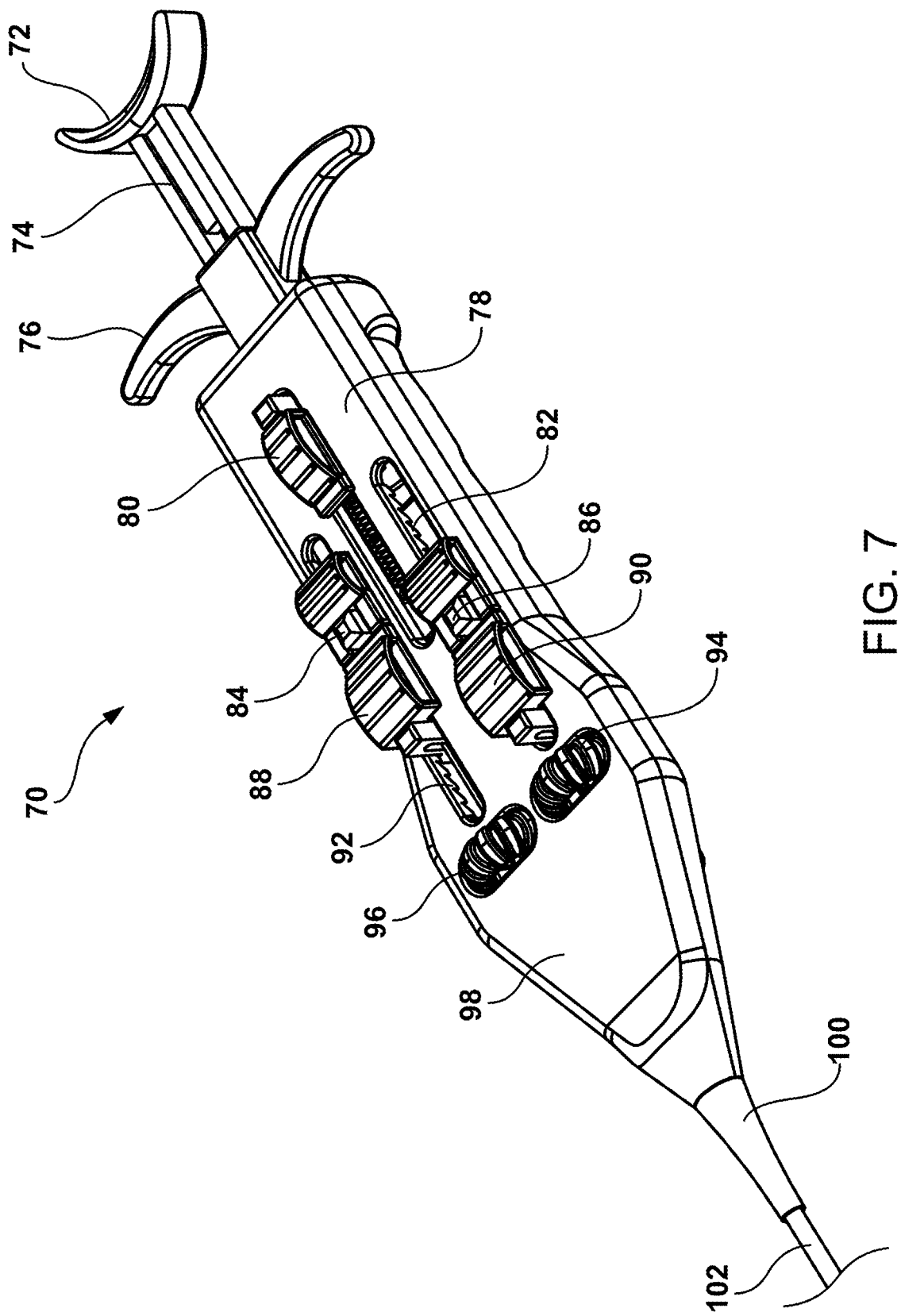
FIG. 7 is a perspective top view of the proximal handle mechanism showing the overall design and configuration of channels.

FIG. 7 is a perspective view of the handle mechanism 70 having a body 78 that comprises a clam shell design. The clam shell design has a top section and a bottom section that felicitate the fabrication and placement of the handle components within the handle mechanism 70. The handle mechanism 70 has a pair of thumbwheels 96, 94 for producing rotational forces to the inner tubular members 114, 116, respectively, and also has distally mounted helical tissue anchors 26, 42. Included is a first slide button 88 for advancing and retracting the first inner tubular member 114, and a first release button 84 for disengaging the first helical tissue anchor 26. Also included is a second slide button 90 for advancing and retracting the second inner tubular member 116, and a second release button 86 for disengaging the second helical tissue anchor 42. Attached and engaged to the distal end of the handle body 78 is the proximal end of the outer sheath 102 with strain release mechanism 100.

The first inner tubular member 114, at the sheath strain relief 100, enters the handle body 78 from its originating distal end, whereby the outer surface of the first inner tubular member 114 is engaged to the first thumbwheel 96, thereby allowing for rotational movement and embedment of the first helical tissue anchor 26. The first inner tubular member 114 is further engaged to the first slide mechanism 88 for advancing and retracting the first tubular member 114 within the sheath and for maneuvering its proximal end with first helical tissue anchor 26, towards the desired treatment site. The first release button 84 is also engaged to the first inner tubular member's stylus for releasing the first helical tissue anchor 26 after embedment in the tissue.

The second inner tubular member 116, at the sheath strain relief 100, enters the handle body 78 from its distal end, whereby the outer surface of the second inner tubular member 116 is engaged to the second thumbwheel 94, thereby allowing for rotational movement for embedment of the second helical tissue anchor 42. The second inner tubular member 116 is further engaged to the second slide mechanism 90 for advancing and retracting the second tubular member 116 within the sheath and for maneuvering its proximal end with second helical tissue anchor 42, towards the desired treatment site. The second release button 86 is also engaged to the second inner tubular member's stylus for releasing the second helical tissue anchor 42 after embedment in the tissue.

The handle body 78, the pair of thumbwheels 94, 96, the pair of slide buttons 86, 88 and the pair or release buttons 84, 86 all can be fabricated from a number of polymeric materials, such as polyvinyl chloride (PVC), polyethylene, polypropylene, PEEK, polybutylene, acrylonitrile-butadiene-styrene (ABS), rubber modified styrene, polyacetal, polyethylene, polyurethane or nylon, or any combination thereof.

FIG. 8 is a perspective top view of the bottom section 106 of the handle mechanism 70 showing the overall design and configuration of channels. In this figure, the upper clam shell component has been removed and a better view of all the internal components is shown. The handle mechanism 70 is a clam shell design that facilitates the assembly process for placing and locating the various components. The upper section and lower section of the clam shell design can be attached to each other using general adhesive, snap fit or screw technology. At the proximal end of the handle mechanism 70 is a proximal retraction member 72 with proximal member shaft 74 and proximal retraction finger grips. Positioned in specific locations are the first, second, third and fourth clam shell connection means 104a, 104b, 104c and 104d. Also positioned in a strategic location is the first and second clam shell alignment tab 110a and 110b. The third slide button 80 is engaged to spring mechanism 108 and the top half of the handle 78, to apply tension to the suture strap mechanism. The single suture strap mechanism 118, enters from the strain relief 100 and is positioned by the alignment bridge 98, and enclosed by the spring mechanism 108 near its connection to the third slide button 80. The proximal section of the first inner tubular member 114 enters from the strain relief 100, is positioned by an alignment bridge 98 to the first tissue anchor thumbwheel 96. The outer surface of the first inner tubular member 114 is engaged to the lumen of the first tissue anchor thumbwheel 96 by adhesive or press fit, such that rotation of the first tissue anchor thumbwheel imparts a likewise rotational force on the first inner tubular member 114 and onward to the first tissue anchor 26. The first inner tubular member 114 is finally engaged to the first slide button 88. The proximal section of the second inner tubular member 116 enters from the strain relief 100, is positioned by an alignment bridge 98 to the second tissue anchor thumbwheel 94. The outer surface of the second inner tubular member 116 is engaged to the lumen of the second tissue anchor thumbwheel 94 by adhesive or press fit, such that rotation of the second tissue anchor thumbwheel 94 imparts a likewise rotational force on the second inner tubular member 116 and onward to the second tissue anchor 42. The second inner tubular member 116 is finally engaged to the second slide button 96.

Figure 9:
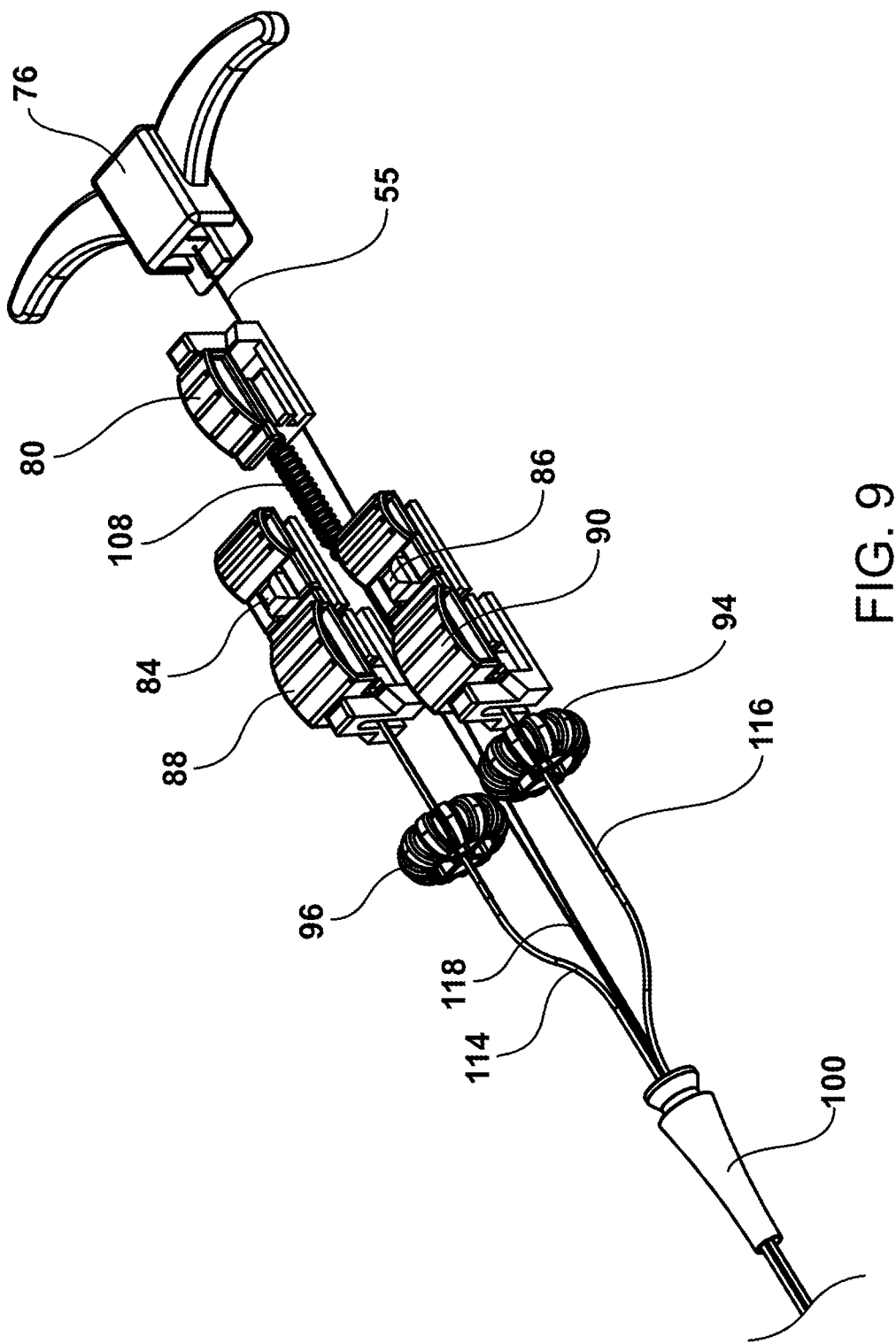
FIG. 9 is a perspective skeleton view of components of the proximal handle mechanism with the top and bottom body members removed, further showing the components and interaction with tubular members.

FIG. 9 is a perspective skeleton view of components of the proximal handle mechanism with the top and bottom body members removed, further showing the main components and interaction with tubular members. Exiting the strain relief 100 are the first inner tubular member 114, the second inner tubular member 116, the tightening member 55 and the single suture strap mechanism 118. Also shown is first inner tubular member 114 passing through, and attached to, a lumen of the first thumbwheel 96, and the second inner tubular member 116 passing through, and attached to, a lumen of the second thumbwheel 94. The terminal end of the first inner tubular member 114 is attached to the first slide 88 and the second inner tubular member 116 is attached to the second slide 90. The single suture strap mechanism 118 passes through a spring mechanism 108 and terminates at third slide mechanism 80, and the tightening member 55 is attached to the proximal retraction handle 76.

Figure 10:
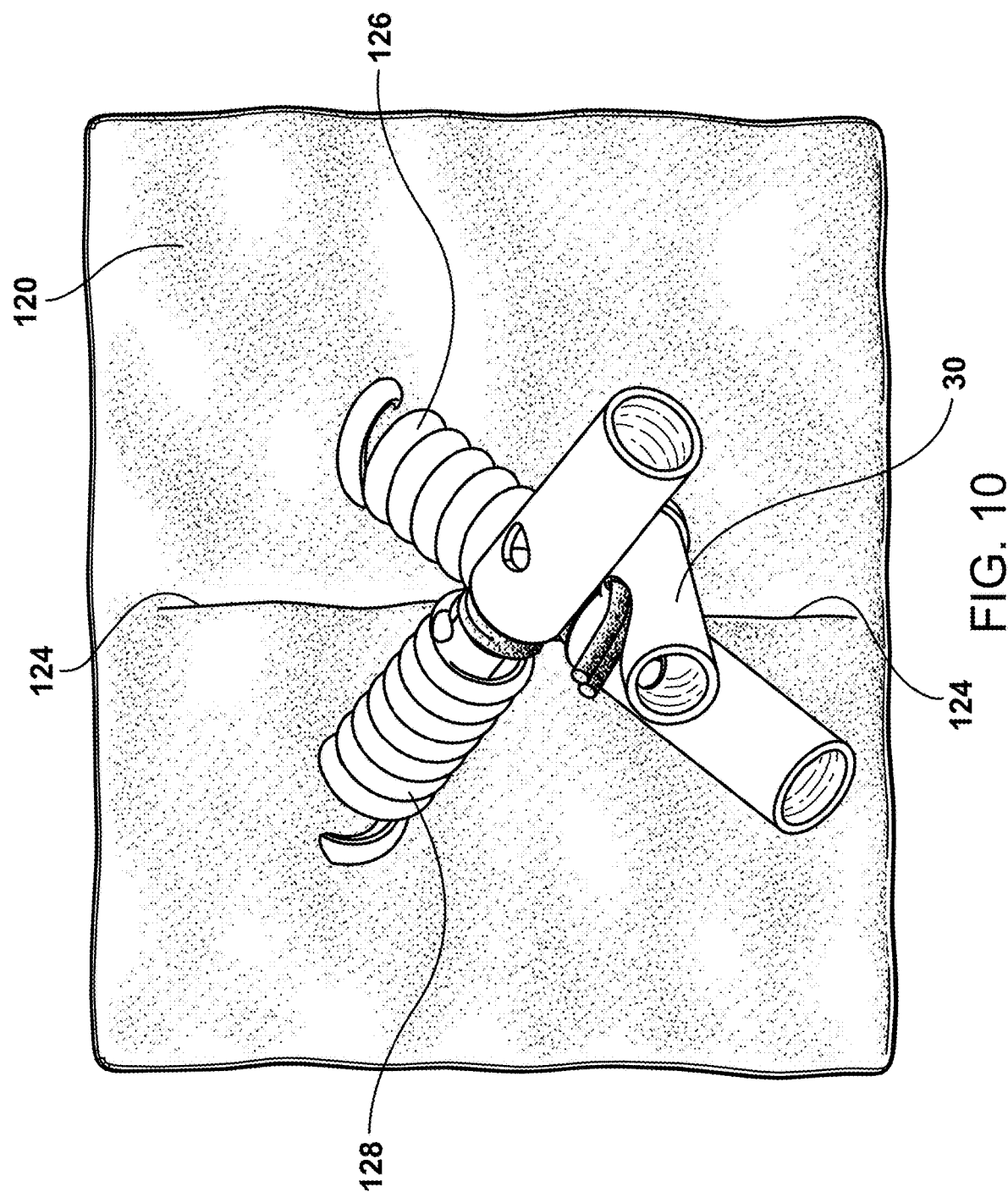
FIG. 10 is a perspective view of the helical tissue anchors and suture delivery components in a clinical setting, whereby a defect in the tissues has been closed by manipulation of the delivery handle controls and retraction of the sutures attached to the two helical tissue anchors embedded within the side area of the tissue defect.

FIG. 10 is a perspective view of a pair of helical tissue anchors 128, 126 and suture delivery components 30 in a clinical setting, whereby a defect 124 in intestinal mucosal, submucosal or muscle tissues has been closed by manipulation of the delivery handle controls and retraction of the sutures attached to the two helical tissue anchors embedded within the side area of the mucosal or muscle tissue defect.

The Applicants anticipate that further developments and embodiments for a tissue anchor and delivery device with multiple tissue anchors in series within a catheter includes a specifically designed apparatus to deploy series of anchors (details not shown in the figures). In this additional embodiment, the tissue anchor(s) are deployed within the catheter in an extended or flat like form, then as they are pushed out of a constraining tube, they immediately curl into a circular or helical-like configuration. Further modifications or embodiments for the tissue anchor device has at least two tissue anchors arranged in series within a catheter, with a suture or suture like material affixed to the first or distal anchor, and then threaded through the eyelets of each following anchor(s). The suture is allowed to slide freely through the following anchors and then the suture extends through the catheter and out the proximal end of the catheter, such that the operator can grasp the end of the suture. A sliding crimp tie is positioned between every two anchors in series along the catheter. Once the first anchor is fired and affixed to tissue, it exits the catheter, suture attached, moving the second anchor, with sliding but attached suture to the forward or distal end of the catheter. Once the second anchor is affixed to tissue, the suture material connects these two affixed anchors and a sliding crimp tie also exits the catheter following the second anchor. The operator grasps the proximal suture end and pulls it, with the crimp tie supported by the distal end of the catheter, and the tie slides such that the anchors become close to each other and fixed in this configuration, whereby a defect would be closed. Two, three, four, or any number of anchors can be deployed in the same manner as described above to close a complex tissue defect.

Operation

The operation steps of the first embodiment for repairing wall defects and lesions are presented below.

Accessing and visualizing the treatment area using standard endoscopy.

Advancing the helical tissue anchor device through the working channel of the endoscope.

To engage one side of the treatment site, advancing one of the thumb slides forward, thereby advancing and locking the first helical device and its delivery catheter out of the distal end of the catheter shaft at a desired length. The first helical device and its delivery catheter can be visualized by the endoscope.

Manipulating the endoscope and first tissue helical anchor and its delivery catheter to position the first tissue helical device against the first attachment target site.

Rotating a first thumbwheel to embed the first tissue helical device into the mucosal, submucosal or muscle tissue as desired.

Pulling back on the first release mechanism to release the first helical device.

Pushing the central button on the first thumb slide to release the thumb slide, thereby allowing it to be pulled proximally.

Retracting the thumb slide back, pulling the delivery catheter back into the sheath of the helical device, thereby leaving the first tissue helical device attached to the suture strap mechanism embedded into the tissue.

To engage the other side of the lesion, advancing and locking the second thumb slide forward, thereby advancing the second helical tissue anchor and its delivery catheter out of the distal end of the catheter shaft at a desired length. The second helical tissue device and its delivery catheter can be visualized by the endoscope.

Manipulating the endoscope and second helical tissue anchor and its delivery catheter to position the second tissue helical device against the second attachment target site.

Rotating the other thumbwheel to embed the second tissue helical device into the mucosal, submucosal or muscle tissue as desired.

Pulling back on the second release mechanism to release the second tissue helical device.

Pushing the central button on the second thumb slide down to release the thumb slide, thereby allowing it to be pulled proximally.

Retracting the thumb slide back, pulling the delivery catheter back into the sheath of the helical device, thereby leaving the second tissue helical device attached to the suture strap mechanism embedded into the tissue.

Advancing the entire device forward, allowing the tensioned suture strap mechanism to pull the suture strap into outer sheath until the two anchors and the tissue defect walls are pulled together, thereby partially or fully closing the tissue defect.

Pulling the proximal retraction finger grips back to initially lock the suture strap into the tightening and excising tubular member.

Continuing to pull on the retraction finger grips to cut the suture strap and release the suture tightening and excising inner tubular member from the tightening member.

The device can then be removed from the endoscope leaving the tissue defect partially or fully closed by the tightened anchors.

In another embodiment of the device, the tightening mechanism could be a separate catheter. In this embodiment, the device is removed from the endoscope once the anchors are placed, thereby leaving suture strap mechanism in the endoscope channel.

By holding the central mandrel fixed and sliding the separate tightening device forward, a cinch, ferrell, bolo tie or spring or knot pushed with a knot pusher is pushed distally, thereby moving and locking the two helical anchors together, so as to partially or fully close the treatment area.

Referring to FIGS. 11-14, an embodiment of the present disclosure further provides another delivery system 10, which is principally the same as the delivery system 10 shown in FIGS. 1-10 in terms of structure, working principle, technical problems solved, and achievable technical effects. The delivery system 10 shown in FIGS. 11-14 will be described below. It should be noted that the biggest difference between the delivery system 10 shown in FIGS. 11-14 and the delivery system 10 shown in FIGS. 1-10 lies in the specific structure of the handle mechanism 70, and the remaining parts are substantially the same. All the components other than the handle mechanism 70 can be understood with reference to FIGS. 1-10 and related text descriptions thereof. Therefore, the following detailed description will focus on the handle mechanism 70.

Figure 13:
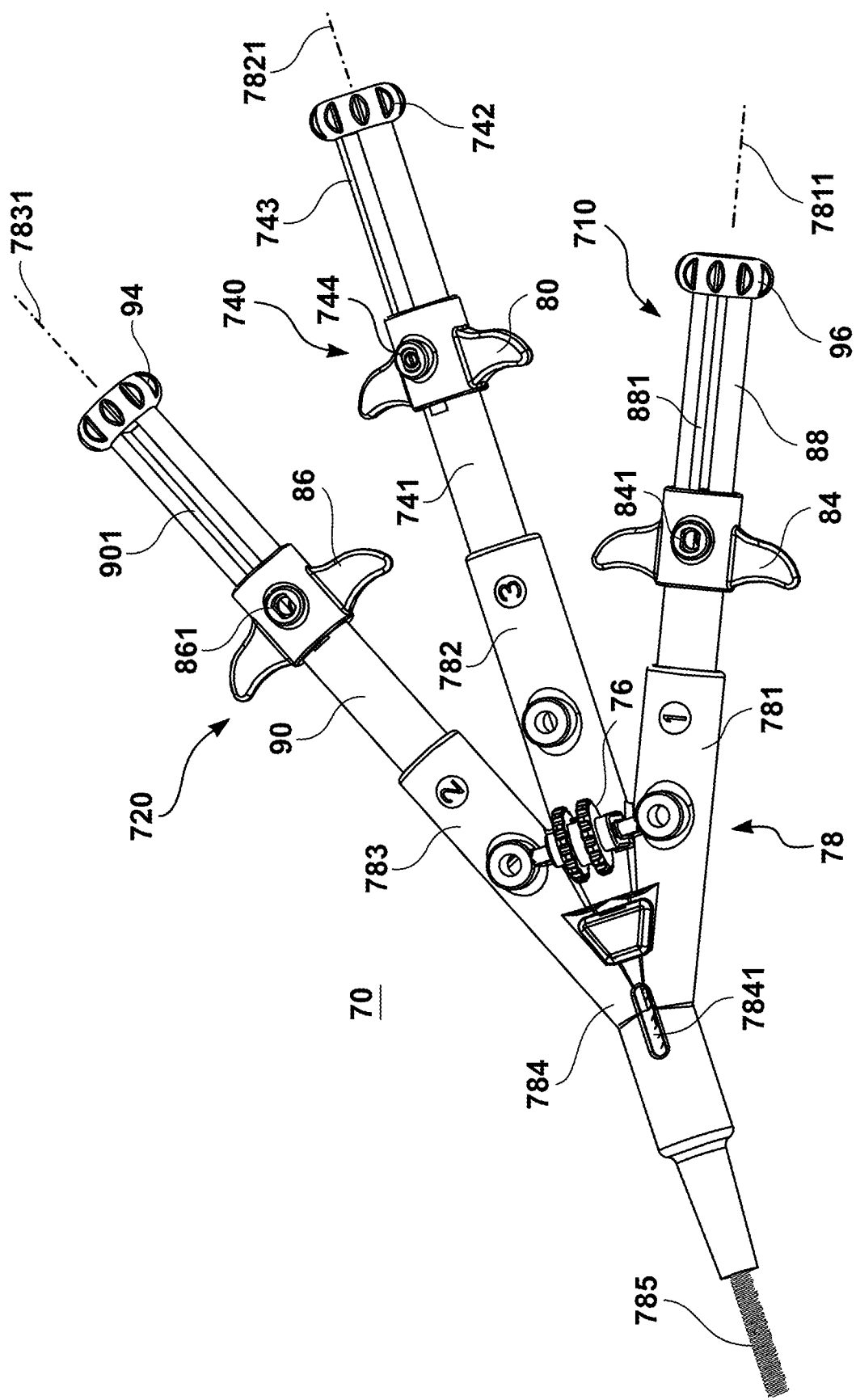
FIG. 13 shows a schematic view of a handle mechanism of FIG. 11.
Figure 14:
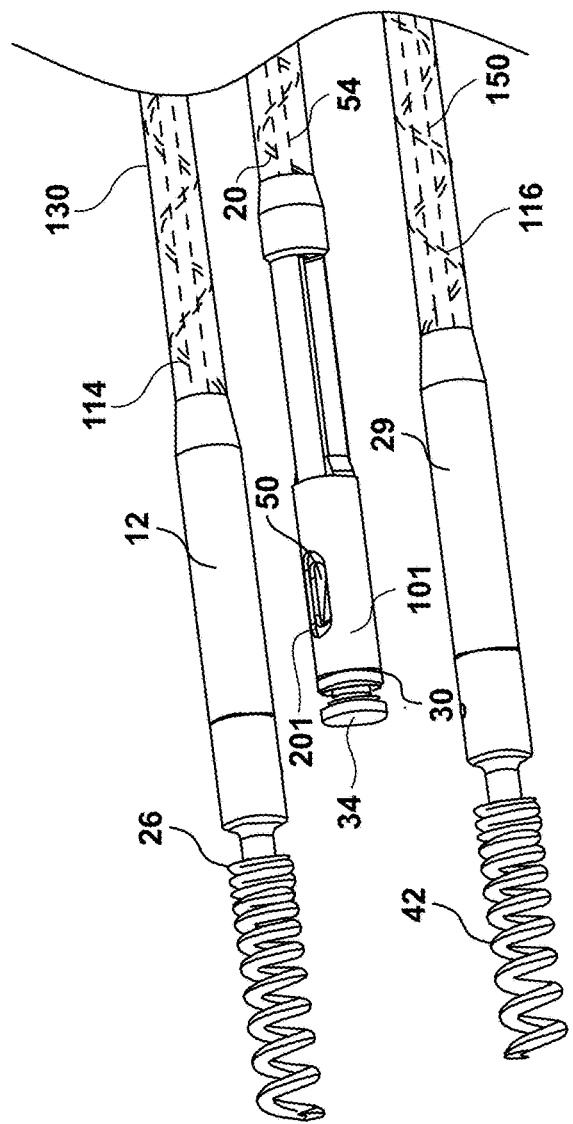
FIG. 14 shows a schematic view of distal sections of the delivery system of FIG. 11.

FIGS. 11 and 12 show the delivery system 10 from different perspectives, which includes a handle mechanism 70 and a multi-lumen catheter 11, among others. FIG. 13 shows details of the handle mechanism 70 and FIG. 14 shows details of the distal sections of the delivery system 10.

The terms "distal end", "proximal end", and the like should be described throughout the text, and the description made here is intended only to provide a better understanding of the present disclosure, and shall not be understood as limiting the present disclosure. Generally, during the use of the delivery system 10, the front end section of the delivery system 10 (which refers to the left end of the delivery system 10 in the relative position in FIG. 11) will be introduced into a human body, while the rear end section of the delivery system 10 (which refers to the right end of the delivery system 10 in the relative position in FIG. 11) remains outside the human body for being operated by a medical staff (e.g., a clinician). Therefore, the "distal end" can be understood as the front end section of a part or component that is relatively close to the human body, and the "proximal end" can be understood as the rear end section of the part or component that is relatively close to the outside of the human body. Naturally, the "proximal end" and "distal end" refer, by default, to the proximal and distal ends of the entire delivery system 10 when they are not clearly indicated as proximal and distal ends of a part or component.

Referring to FIG. 13, the handle mechanism 70 shown in FIG. 13 includes:

a body 78;

a first anchor delivery device 710 provided to the body 78, wherein the first anchor delivery device 710 is configured to control a first tissue anchor 26, so that the first tissue anchor 26 is anchored into a tissue and released;

a second anchor delivery device 720 provided to the body 78, wherein the second anchor delivery device 720 is configured to control a second tissue anchor 42, so that the second tissue anchor 42 is anchored into a tissue and released;

a tightening device (cinching device) 730 provided to the body 78, wherein the tightening device 730 is configured to pull a suture member 32 to tighten (cinch) the first tissue anchor 26 and the second tissue anchor 42 connected to the suture member 32; and a locking and cutting device 740 provided to the body 78, wherein the locking and cutting device 740 is configured to lock the suture member 32 to an inner tubular member 30, cut the suture member 32, and completely release the inner tubular member 30 and a portion of the suture member 32 connected to the inner tubular member 30.

It should be noted that the components such as "first tissue anchor 26", "second tissue anchor 42", "suture member 32", and "inner tubular member 30" mentioned here may be formed with reference to the structures shown in FIGS. 1-10. The "handle mechanism 70" mentioned here may be formed with reference to FIGS. 7 and 13. The first anchor delivery device 710, the second anchor delivery device 720, the tightening device 730, and the locking and cutting device 740 of the handle mechanism 70 can be operated independently of one another. For example, the first tissue anchor 26 can be anchored into the tissue and released by operating the first anchor delivery device 710, the second tissue anchor 42 can be anchored into the tissue and released by operating the second anchor delivery device 720, the suture member 32 can be tightened by operating the tightening device 730, and the suture member 32 and the inner tubular member 30 can be locked and released by cutting the suture member 32 by operating the locking and cutting device 740. Here, a description can be made using the relative position in FIG. 10 with reference to FIG. 10. The first tissue anchor 26 (126) is anchored into a first target tissue on the right, and the second tissue anchor 42 (128) is anchored into a second target tissue on the left, wherein the first target tissue and the second target tissue are separated by a defect 124. The two tissue anchors are anchored into the two separated target tissues, and then the two tissue anchors can be tightened by tightening the suture member 32, whereby the two target tissues are allowed to be close to each other, so that the defect 124 is closed. Then the suture member 32 is cut off, so that the first tissue anchor 26, the second tissue anchor 42, and a portion of the suture member 32 are released. In this way, the two target tissues are firmly tightened, and the defect 124 is always in the closed state.

In this embodiment, a total of two anchor delivery devices, i.e., the first anchor delivery device 710 and the second anchor delivery device 720, are disclosed. In other embodiments, the number of anchor delivery devices is not limited. In other words, three or more anchor delivery devices may be provided. The specific structure of the first anchor delivery device 710 will be described in detail below. In this embodiment, the two anchor delivery devices have substantially the same structures, therefore the second anchor delivery device 720 will not be described in detail. Naturally, the two anchor delivery devices may have different structures in other embodiments.

In a first example, referring to FIG. 13, the first anchor delivery device 710 includes a first slide 88 and a first release button 84. The first slide 88 is configured to be connected to a first elongated shaft 114 and a first inner tubular member 130, and the first slide 88 is slidably connected to the body 78 to drive the first elongated shaft 114 and the first inner tubular member 130 to move. The first release button 84 is configured to be connected to the first elongated shaft 114, and the first release button 84 is slidably connected to the body 78 to drive the first elongated shaft 114 to move.

Here, the first elongated shaft 114 is movably threaded (or passed) through the first inner tubular member 130, a first engagement member 12 is connected to the distal end of the first inner tubular member 130, the first tissue anchor 26 is connected to the distal end of the first elongated shaft 114, and the first tissue anchor 26 is removably connected to the first engagement member 12. When the first tissue anchor 26 is engaged with the first engagement member 12 and the first slide 88 is moved distally, the first tissue anchor 26 and the first engagement member 12 are moved distally, and the action of the first elongated shaft 114 enables the first tissue anchor 26 to be in contact with and anchored into tissue. When the first slide 88 is positionally unchanged relative to the body 78 and the first release button 84 is moved proximally, the first engagement member 12 is disengaged from the first tissue anchor 26 and the first tissue anchor 26 is released.

It should be noted that this "first tissue anchor 26" may be a piercing tissue anchor (similar to an anchor with a hook). While the first slide 88 is being operated to move distally, the first tissue anchor 26 is moved distally, and the action of the first elongated shaft 114 enables the first tissue anchor 26 to contact and pierce into tissue. When the position of the first slide 88 is kept unchanged and the first release button 84 is moved proximally, the first engagement member 12 is disengaged from the first tissue anchor 26 and the first tissue anchor 26 is released. At this time, the first tissue anchor 26 is retained on the tissue because it hooks the tissue.

In a second example, on the basis of the first example, the first slide 88 is rotatably connected to the body 78 to drive the first elongated shaft 114 to rotate, wherein when the first slide 88 is rotated relative to the body 78, the action of the first elongated shaft 114 enables the first tissue anchor 26 to be in contact with and rotationally anchored into the tissue.

It should be noted that this "first tissue anchor 26" may be a rotary anchorable tissue anchor.

In a third example, referring to FIG. 13, the first anchor delivery device 710 includes a first slide 88, a first thumbwheel 96, and a first release button 84. The first slide 88 is configured to be connected to the first elongated shaft 114 and the first inner tubular member 130, and the first slide 88 is slidably connected to the body 78 to drive the first elongated shaft 114 and the first inner tubular member 130 to move. The first thumbwheel 96 is configured to be connected to the first elongated shaft 114, and the first thumbwheel 96 is rotatably connected to the body 78 to drive the first elongated shaft 114 to rotate. The first release button 84 is configured to be connected to the first elongated shaft 114, and the first release button 84 is slidably connected to the body 78 to drive the first elongated shaft 114 to move.

Here, the first elongated shaft 114 is movably threaded through the first inner tubular member 130, a first engagement member 12 is connected to the distal end of the first inner tubular member 130, the first tissue anchor 26 is connected to the distal end of the first elongated shaft 114, and the first tissue anchor 26 is removably connected to the first engagement member 12. When the first tissue anchor 26 is engaged with the first engagement member 12 and the first slide 88 is moved distally, the first tissue anchor 26 and the first engagement member 12 are moved distally. When the first thumbwheel 96 is rotated relative to the body 78, the action of the first elongated shaft 114 enables the first tissue anchor 26 to be in contact with and rotationally anchored into the tissue. When the first slide 88 is positionally unchanged relative to the body 78 and the first release button 84 is moved proximally, the first engagement member 12 is disengaged from the first tissue anchor 26 and the first tissue anchor 26 is released.

It should be noted that this "first tissue anchor 26" may be a rotary anchorable tissue anchor. The first elongated shaft 114 is movably threaded through the first inner tubular member 130, and the first inner tubular member 130 is movably threaded in the multi-lumen catheter 11. When a medical staff operates the first slide 88, the first thumbwheel 96, and the first release button 84, these components drive the first elongated shaft 114 and the first inner tubular member 130 to move. As a result, the first tissue anchor 26 is rotationally anchored into tissue and the first tissue anchor 26 is released.

It can be understood with reference to the above description that the rotary anchorable tissue anchor has a structure, which is similar to a spring structure and has a sharp distal end, so that it pierces into tissue when it is in contact with and moved toward the tissue, and it is spirally screwed into the tissue during rotation, wherein the number of rotations can determine, to some extent, the depth at which the distal end of the tissue anchor is inserted into the tissue. When the tissue anchor is released, the tissue anchor is retained on the tissue because it is screwed into the tissue. The piercing tissue anchor, when in contact with and moved toward the tissue, pierces into tissue at a depth that is determined, to some extent, by a distance by which the first slide 88 is moved distally. When the tissue anchor is released, the tissue anchor is retained on the tissue because the tissue is hooked by its hook portion.

Specifically, the first thumbwheel 96 is fixed to the proximal end of the first slide 88. This facilitates the operation of the first thumbwheel 96. Moreover, when the first release button 84 is operated to move proximally, the first thumbwheel 96 can abut against and provide support for the palm of the hand of the medical staff, because it is located at the proximal end of the first slide 88. In other embodiments, the first thumbwheel 96 may be mounted at the middle or distal end of the first slide 88. The entire first anchor delivery device 710 has a more compact structure when the first thumbwheel is mounted at the proximal end of the first slide 88 as in this embodiment. In other embodiments, the first thumbwheel 96 and the first slide 88 may be molded and manufactured in one piece. In other words, the two components are integrally formed, alternatively, the outer wall of the first slide 88 is provided with a concavo-convex uneven surface to facilitate operation by the medical staff, wherein the concavo-convex uneven portion is called the first thumbwheel 96. Therefore, the form of arrangement of the first thumbwheel 96 is not limited. The first elongated shaft 114 may also be rotated by directly rotating the first slide 88, then the above-mentioned technical effect can be achieved regardless of whether the first thumbwheel 96 is provided.

Specifically, the first release button 84 is slidably connected to the first slide 88. The first release button 84 has two flaps for being operated by the medical staff. Moreover, the first release button 84 is mounted directly on the first slide 88, so that the first anchor delivery device 710 has a more compact structure. The sliding connection manner is not limited here. For example, the first release button 84 is provided with a slider, the first slide 88 is provided with a sliding slot, and the slider is slidably fitted in the sliding slot to achieve the sliding connection. Alternatively, the first release button 84 is provided with a sliding slot, the first slide 88 is provided with a slider, and the slider is slidably fitted in the sliding slot to achieve the sliding connection.

In this embodiment, the first slide 88 is rod-shaped, the first slide 88, at its distal end, is slidably and rotatably connected to the body 78, and the first release button 84 is sleeved on the first slide 88. The first release button 84 mounted around the first slide 88 allows a smoother and more stable operation. Moreover, the first slide 88 is slidable and rotatable relative to the body 78. In other words, the first tissue anchor 26 is moved close to or away from the tissue while the first slide is sliding, and the first tissue anchor 26 is anchored into the tissue while the first slide is rotating.

Moreover, in this embodiment, the first slide 88 is provided with a first sliding slot 881, and the first release button 84 is slidably fitted with the first sliding slot 881. In other words, a stable sliding effect is achieved by the first release button 84 fitted with the first sliding slot 881.

Specifically, the first thumbwheel 96 is fixed to the proximal end of the first slide 88. The proximal end of the first sliding slot 881 extends to the first thumbwheel 96, and the distal end of the first sliding slot 881 extends to the middle of the first slide 88. A first fastener 841 is fixedly connected to the first release button 84, and the first fastener 841 is slidably fitted with the first sliding slot 881.

The first fastener 841 may be a screw, by which the first release button 84 is restrictively mounted onto the first slide 88, and which is slidably threaded into the first sliding slot 881. In this way, the first release button 84 is slidable more stably, and at the same time, the stroke of the first release button 84 can be limited to some extent. In other words, the first release button 84 is movable only within the range of extension of the first sliding slot 881. In this embodiment, the proximal end of the first elongated shaft 114 is fixedly connected to the first fastener 841. It should be noted that in other embodiments, the proximal end of the first elongated shaft 114 may be fixedly connected directly to the first release button 84.

Referring to FIG. 13, a first axis 7811 (shown by a dashed line) is shown here. In this embodiment, the first slide 88 slides relative to the body 78 in a direction the same as the first axis 7811, and the first slide 88 rotates relative to the body 78 about a shaft axis coinciding with the first axis 7811. The first release button 84 slides relative to the first slide 88 in a direction the same as the first axis 7811.

In this embodiment, the second anchor delivery device 720 has substantially the same structure as the first anchor delivery device 710. In other words, the second anchor delivery device 720 includes substantially the same parts and components, i.e., a second slide 90, a second thumbwheel 94, and a second release button 86, as those of the first anchor delivery device 710. Similarly, the second slide 90 has a second sliding slot 901, and the second release button 86 is slidably fitted with the second sliding slot 901 by means of a second fastener 861. Therefore, related details of the second anchor delivery device 720 can be understood with reference to the first anchor delivery device 710 described above and will not be described in detail here.

When the medical staff operates the first anchor delivery device 710 and the second anchor delivery device 720 to anchor the first tissue anchor 26 and the second tissue anchor 42 into tissues and release them, it is necessary to pull the suture member 32 to tighten (cinch) the first tissue anchor 26 and the second tissue anchor 42, so that the first target tissue and the second target tissue abut closely against each other, whereby the defect 124 is closed. A device for operating the suture member 32 will be described in detail below.

Referring to FIGS. 12 and 13, the tightening device 730 includes a rotary wheel 76 that is rotatably connected to the body 78, and the proximal end of the suture member 32 is wound around the rotary wheel 76. By rotating the rotary wheel 76, the suture member 32 can be moved proximally to tighten the first tissue anchor 26 and the second tissue anchor 42.

During specific use, a distal movement of the suture member 32 is generally not allowed. Therefore, in this embodiment, the tightening device 730 further includes a pawl 761. The pawl 761 is connected to the body 78 at one end thereof and fitted with the rotary wheel 76 at the other end thereof, and the pawl 761 and the rotary wheel 76 constitute a ratchet mechanism. The suture member 32 is moved proximally when the rotary wheel 76 rotates forward, and the rotary wheel 76 is locked by the pawl 761 when the rotary wheel 76 rotates reversely. The pawl 761 is configured such that the rotary wheel 76 is allowed to rotate only in a forward direction to cause a proximal movement of the suture member 32 rather than a distal movement of the suture member 32.

Generally, the suture member 32 will be movably threaded through the multi-lumen catheter 11 and then drawn out at the proximal section of the delivery system 10 (i.e., the body 78), in order to facilitate an operation without affecting the normal use of other devices during the operation. Therefore, in this embodiment, the proximal end of the body 78 is provided with a threading hole 7841. The proximal end of the suture member 32 is threaded inside the body 78 and extended from the body 78 through the threading hole 7841 and wound around the rotary wheel 76.

Generally, after the first tissue anchor 26 and the second tissue anchor 42 are tightened, it is necessary to cut off the suture member 32 connecting the first tissue anchor 26 and the second tissue anchor 42 together, so that the remaining portion of the cut suture member 32 as well as the first tissue anchor 26 and the second tissue anchor 42 connected to this portion of the suture member 32 are integrally released and left in the human body. In this way, it can be ensured that the first target tissue and the second target tissue are always in a state where they abut closely against each other. In other words, the defect 124 is always in the closed state. The device for operating the suture member 32 will be described in detail below.

Referring to FIGS. 13 and 14, the locking and cutting device 740 includes an intermediary slide 741 and a third slide button 80. The intermediary slide 741 is configured to be connected to a third connection shaft 54 and a third intermediary inner tubular member 20, and the intermediary slide 741 is slidably connected to the body 78 to drive the third connection shaft 54 and the third intermediary inner tubular member 20 to move. The third slide button 80 is configured to be connected to the third connection shaft 54, and the third slide button 80 is slidably connected to the body 78 to drive the third connection shaft 54 to move.

Here, the third connection shaft 54 is movably threaded through the third intermediary inner tubular member 20. An inner tubular member 30 is removably connected to the distal end of the third intermediary inner tubular member 20, and a slidable tubular member 101 is slidably sleeved on the inner tubular member 30. The slidable tubular member 101 has a first window 201, and the inner tubular member 30 has a second window 50. A retraction ball mechanism 36 is connected to the distal end of the third connection shaft 54, the retraction ball mechanism 36 is removably threaded in a distal cap 34, and the distal cap 34 is located at the distal end of the inner tubular member 30. The two distal ends of the suture member 32 are connected to the first tissue anchor 26 and the second tissue anchor 42, respectively, and the suture member 32 passes through the distal end of the inner tubular member 30 and passes sequentially through the second window 50 and the first window 201 and then extends to the proximal end. When the intermediary slide 741 slides distally, the third intermediary inner tubular member 20 and the inner tubular member 30 are moved distally at the same time. While the intermediary slide 741 is positionally unchanged relative to the body 78 and the third slide button 80 is moving proximally, the retraction ball mechanism 36 first drives the distal cap 34 to lock the suture member 32 to the inner tubular member 30, and then continues to drive the slidable tubular member 101 to move proximally, so that the first window 201 and the second window 50 cooperatively cut the suture member 32, and then the inner tubular member 30, the distal cap 34 connected to the inner tubular member 30, and a portion of the suture member 32 are completely released.

It should be noted that the third connection shaft 54 is movably threaded through the third intermediary inner tubular member 20, and the third intermediary inner tubular member 20 is movably threaded in the multi-lumen catheter 11. When the medical staff operates the intermediary slide 741 and the third slide button 80, these components drive the third connection shaft 54 and the third intermediary inner tubular member 20 to move. As a result, the first tissue anchor 26 and the second tissue anchor 42 are tightened by the cut portion of the suture member 32, and at the same time this portion of the suture member 32 is locked by the distal cap 34 and the inner tubular member 30.

In this embodiment, the third slide button 80 is slidably connected to the intermediary slide 741 in order to provide a more compact structure for the entire locking and cutting device 740. Naturally, in other embodiments, the third slide button 80 may be mounted on the body 78.

In this embodiment, the intermediary slide 741 is rod-shaped, the intermediary slide 741, at its distal end, is slidably connected to the body 78, and the third slide button 80 is sleeved on the intermediary slide 741. The third slide button 80, mounted as a sleeve, is slidable more stably and smoothly.

In order to facilitate operation and to restrict the stroke of the third slide button 80, this embodiment is designed in such a manner that an intermediary thumbwheel 742 is connected to the proximal end of the intermediary slide 741, the intermediary slide 741 is provided with an intermediary sliding slot 743 having a proximal end extending to the intermediary thumbwheel 742 and a distal end extending to the middle of the intermediary slide 741, and an intermediary fastener 744 slidably fitted with the intermediary sliding slot 743 is fixedly connected to the third slide button 80.

It should be noted that the intermediary fastener 744 may be a screw. In other words, the screw is slidably threaded in the intermediary sliding slot 743 to restrict the stroke of the third slide button 80.

Referring to FIG. 13, a third axis 7821 (shown by a dashed line) is shown here. In this embodiment, the intermediary slide 741 slides relative to the body 78 in a direction the same as the third axis 7821, and the third slide button 80 slides relative to the intermediary slide 741 in a direction the same as the third axis 7821.

Referring again to FIG. 13, in this embodiment, the body 78 includes a first sleeve 781, an intermediary sleeve 782, a second sleeve 783, and a junction section 784. The distal end of the first sleeve 781, the distal end of the intermediary sleeve 782, and the distal end of the second sleeve 783 are all connected to the proximal end of the junction section 784, and the distal end of the junction section 784 is configured to be connected to the multi-lumen catheter 11. The first anchor delivery device 710 is assembled with the first sleeve 781, the second anchor delivery device 720 is assembled with the second sleeve 783, the locking and cutting device 740 is assembled with the intermediary sleeve 782, and the tightening device 730 is assembled with the junction section 784.

Here, the first anchor delivery device 710 is configured to control the first tissue anchor 26 by means of the multi-lumen catheter 11. The second anchor delivery device 720 is configured to control the second tissue anchor 42 by means of the multi-lumen catheter 11. The tightening device 730 is configured to pull the suture member 32 through the multi-lumen catheter 11. The locking and cutting device 740 is configured to lock the suture member 32 to the inner tubular member 30, cut the suture member 32, and completely release the inner tubular member 30 and a portion of the suture member 32 connected to the inner tubular member 30 by means of the multi-lumen catheter 11.

It should be noted that the first elongated shaft 114, the first inner tubular member 130, the second elongated shaft 116, the second inner tubular member 150, the third connection shaft 54, the third intermediary inner tubular member 20, and the suture member 32 described above are all threaded in the multi-lumen catheter 11, so that the multi-lumen catheter 11 can restrain these components.

In this embodiment, the distal end of the first anchor delivery device 710 is movably disposed in the first sleeve 781, the distal end of the locking and cutting device 740 is movably disposed in the intermediary sleeve 782, and the distal end of the second anchor delivery device 720 is movably disposed in the second sleeve 783, in order to restrain the movement strokes of the first anchor delivery device 710, the locking and cutting device 740, and the second anchor delivery device 720. It can be understood that the first anchor delivery device 710, the locking and cutting device 740, and the second anchor delivery device 720 are all disposed in the corresponding sleeves. In other embodiments, the first anchor delivery device 710, the locking and cutting device 740, and the second anchor delivery device 720 may be mounted around the corresponding sleeves.

Referring to FIG. 13, in this embodiment, the three sleeves are provided relatively independently of one another, i.e., in a three-branch design, in order to facilitate operation by a medical staff. For example, the first axis 7811 of the first sleeve 781 and the second axis 7831 of the second sleeve 783 are distributed at an acute angle, and the third axis 7821 of the intermediary sleeve 782 is located between the first axis 7811 and the second axis 7831. The first axis 7811 and the second axis 7831 may be distributed at an angle of 30° to 60°, and the third axis 7821 is located exactly centrally between the first axis 7811 and the second axis 7831, thus the overall structure is well symmetrical.

In this embodiment, the body 78 further includes a spring tube 785 having a proximal end connected to the distal end of the junction section 784 and a distal end configured to be coupled to the multi-lumen catheter 11, so that the entire delivery system 10 has a certain flexibility and is conveniently rotatable as a whole, for example.

In this embodiment, the rotary wheel 76 rotates about a shaft axis perpendicular to the third axis 7821 of the intermediary sleeve 782, in order to facilitate an operation of the rotary wheel 76 by the medical staff.

This embodiment also provides an operation method, which is implemented using the handle mechanism 70 described above. The operation method includes:

accessing and visualizing a treatment area using an endoscope; delivering the distal ends of the first tissue anchor 26, the second tissue anchor 42, the inner tubular member 30, and the suture member 32 to the distal end of the endoscope through the working channel of the endoscope;

operating the first anchor delivery device 710 to anchor the first tissue anchor 26 into the first target tissue and release the first tissue anchor 26;

operating the second anchor delivery device 720 to anchor the second tissue anchor 42 into the second target tissue and release the second tissue anchor 42;

operating the tightening device 730 to pull the suture member 32 and tighten the first tissue anchor 26 and the second tissue anchor 42 connected to the suture member 32, so as to tighten the first target tissue and the second target tissue; and operating the locking and cutting device 740 to lock the suture member 32 to the inner tubular member 30, cut the suture member 32, and completely release the inner tubular member 30 and a portion of the suture member 32 connected to the inner tubular member 30.

Specifically, in one example, an example is given after the delivery system 10 is installed. In an operation procedure, generally, an endoscope is first inserted into the human body, and then the entire distal section of the delivery system 10 is delivered through the working channel of the endoscope to the target position.

In step 1, the first tissue anchor 26 is fired. Specifically, the first slide 88 is pushed to move proximally, thereby driving the first inner tubular member 130 and the first elongated shaft 114 to move proximally. At this time, the first tissue anchor 26 is in contact with the first target tissue. Then, the position of the first slide 88 is kept unchanged, and the first thumbwheel 96 is rotated so as to drive the first elongated shaft 114 to rotate, so that the first tissue anchor 26 connected to its distal end is rotated and anchored into the first target tissue. When the first tissue anchor is anchored in place, the position of the first slide 88 is kept unchanged, and the first release button 84 is pushed to move distally, thereby driving the first elongated shaft 114 to move distally. During its movement, the first elongated shaft 114 is disengaged from the first tissue anchor 26, and at the same time the first engagement member 12 fixed to the distal end of the first inner tubular member 130 is disengaged from the first tissue anchor 26, whereby the release of the first tissue anchor 26 is accomplished.

In step 2, the second tissue anchor 42 is fired. Specifically, the second tissue anchor 42 is anchored into the second target tissue and released (Specific operations can be understood with reference to step 1).

In step 3, the suture member 32 is tightened. Specifically, the rotary wheel 76 is rotated so that the suture member 32 is moved proximally to tighten the first tissue anchor 26 and the second tissue anchor 42 at the distal position thereof.

In step 4, the suture member 32 is cut and the corresponding components are released. Specifically, the intermediary slide 741 is pushed to move distally while continuing to operate the rotary wheel 76 to tighten the suture member 32, so as to further tighten the first tissue anchor 26 and the second tissue anchor 42. When the inner tubular member 30 reaches the required position, the position of the intermediary slide 741 is kept unchanged, and the third slide button 80 is pulled to move proximally so that the retraction ball mechanism 36 connected to the distal end of the third connection shaft 54 is continuously moved proximally. During the movement, first the distal cap 34 is driven to move proximally so that the distal cap 34 snaps into the distal end of the inner tubular member 30, and at the same time the suture member 32 passing through the distal end of the inner tubular member 30 is locked tightly. The third connection shaft 54 continues to move proximally, so that the retraction ball mechanism 36 is disengaged from the distal cap 34, and then the slidable tubular member 101 is driven to move proximally. At this time, the first window 201 and the second window 50 cooperate with each other to cut off the suture member 32 while the slidable tubular member 101 is moving proximally, because the suture member 32 extends proximally through the second window 50 and the first window 201 sequentially. Then, the third connection shaft 54 continues to move proximally, so that the inner tubular member 30 is disengaged from the third intermediary inner tubular member 20.

In step 5, the body 78 is pulled to extract the third intermediary inner tubular member 20, the first inner tubular member 130, and the second inner tubular member 150 together with the multi-lumen catheter 11 through the working channel of the endoscope, so that the first tissue anchor 26, the second tissue anchor 42, the inner tubular member 30, the distal cap 34, and the partially cut suture member 32 connecting these components are completely released.

While the present disclosure has been described as having a preferred design, the present disclosure can be further modified within the spirit and scope of the present disclosure. The application is therefore intended to cover any variations, uses, or adaptations of the present disclosure using its general principles. Further, this application is intended to cover such departures from the present disclosure as come within known or customary practice and the art to which the present disclosure pertains and which fall within the limits of the appended claims.

What is claimed is:
1. A handle mechanism, comprising:
a body;

a first anchor delivery device provided to the body, wherein the first anchor delivery device is configured to control a first tissue anchor, so that the first tissue anchor is anchored into a tissue and released;

a second anchor delivery device provided to the body, wherein the second anchor delivery device is configured to control a second tissue anchor, so that the second tissue anchor is anchored into a tissue and released;

a tightening device provided to the body, wherein the tightening device is configured to pull a suture member to tighten the first tissue anchor and the second tissue anchor connected to the suture member; and a locking and cutting device provided to the body, wherein the locking and cutting device is configured to lock the suture member to an inner tubular member, cut the suture member, and completely release the inner tubular member and a portion of the suture member connected to the inner tubular member.

2. The handle mechanism according to claim 1, wherein the first anchor delivery device comprises a first slide and a first release button, wherein the first slide is configured to be connected to a first elongated shaft and a first inner tubular member, and the first slide is slidably connected to the body to drive the first elongated shaft and the first inner tubular member to move; and the first release button is configured to be connected to the first elongated shaft, and the first release button is slidably connected to the body to drive the first elongated shaft to move, wherein the first elongated shaft is movably threaded through the first inner tubular member, a first engagement member is connected to a distal end of the first inner tubular member, the first tissue anchor is connected to a distal end of the first elongated shaft, and the first tissue anchor is removably connected to the first engagement member, wherein when the first tissue anchor is engaged with the first engagement member and the first slide is moved distally, the first tissue anchor and the first engagement member are moved distally, and an action of the first elongated shaft enables the first tissue anchor to be in contact with and anchored into the tissue; and when the first slide is positionally unchanged relative to the body and the first release button is moved proximally, the first engagement member is disengaged from the first tissue anchor and the first tissue anchor is released.

3. The handle mechanism according to claim 2, wherein the first slide is rotatably connected to the body to drive the first elongated shaft to rotate, wherein when the first slide is rotated relative to the body, the action of the first elongated shaft enables the first tissue anchor to be in contact with and rotationally anchored into the tissue.

4. The handle mechanism according to claim 2, wherein the first anchor delivery device further comprises a first thumbwheel, wherein the first thumbwheel is configured to be connected to the first elongated shaft, and the first thumbwheel is rotatably connected to the body to drive the first elongated shaft to rotate, wherein when the first thumbwheel is rotated relative to the body, the action of the first elongated shaft enables the first tissue anchor to be in contact with and rotationally anchored into the tissue.

5. The handle mechanism according to claim 4, wherein the first thumbwheel is fixed to a proximal end of the first slide.

6. The handle mechanism according to claim 4, wherein the first release button is slidably connected to the first slide.

7. The handle mechanism according to claim 6, wherein the first slide is rod-shaped, the first slide, at its distal end, is slidably and rotatably connected to the body, and the first release button is sleeved on the first slide.

8. The handle mechanism according to claim 7, wherein the first slide is provided with a first sliding slot, and the first release button is slidably fitted with the first sliding slot.

9. The handle mechanism according to claim 1, wherein the tightening device comprises a rotary wheel, wherein the rotary wheel is rotatably connected to the body, and a proximal end of the suture member is wound around the rotary wheel.

10. The handle mechanism according to claim 9, wherein the tightening device further comprises a pawl, wherein the pawl has one end connected to the body and the other end fitted with the rotary wheel, and the pawl and the rotary wheel constitute a ratchet mechanism, the suture member is moved proximally when the rotary wheel rotates forward, and the rotary wheel is locked by the pawl when the rotary wheel rotates reversely.

11. The handle mechanism according to claim 9, wherein a proximal end of the body is provided with a threading hole, and the proximal end of the suture member is threaded inside the body, extended from the body through the threading hole and wound around the rotary wheel.

12. The handle mechanism according to claim 1, wherein the locking and cutting device comprises an intermediary slide and a third slide button, wherein the intermediary slide is configured to be connected to a third connection shaft and a third intermediary inner tubular member, and the intermediary slide is slidably connected to the body to drive the third connection shaft and the third intermediary inner tubular member to move; and the third slide button is configured to be connected to the third connection shaft, and the third slide button is slidably connected to the body to drive the third connection shaft to move, wherein the third connection shaft is movably threaded through the third intermediary inner tubular member, the inner tubular member is removably connected to a distal end of the third intermediary inner tubular member, and a slidable tubular member is slidably sleeved on the inner tubular member, the slidable tubular member has a first window, and the inner tubular member has a second window; a retraction ball mechanism is connected to a distal end of the third connection shaft, wherein the retraction ball mechanism is removably threaded in a distal cap, and the distal cap is located at a distal end of the inner tubular member; the two distal ends of the suture member are connected to the first tissue anchor and the second tissue anchor, respectively, and the suture member passes through the distal end of the inner tubular member and passes sequentially through the second window and the first window and then extends to a proximal end; when the intermediary slide slides distally, the third intermediary inner tubular member and the inner tubular member are moved distally at the same time; and while the intermediary slide is positionally unchanged relative to the body and the third slide button is moving proximally, the retraction ball mechanism first drives the distal cap to lock the suture member to the inner tubular member, and then continues to drive the slidable tubular member to move proximally, so that the first window and the second window cooperatively cut the suture member, and then the inner tubular member, the distal cap connected to the inner tubular member, and a portion of the suture member are completely released.

13. The handle mechanism according to claim 12, wherein the third slide button is slidably connected to the intermediary slide.

14. The handle mechanism according to claim 13, wherein the intermediary slide is rod-shaped, the intermediary slide, at its distal end, is slidably connected to the body, and the third slide button is sleeved on the intermediary slide.

15. The handle mechanism according to claim 13, wherein an intermediary thumbwheel is connected to a proximal end of the intermediary slide, the intermediary slide is provided with an intermediary sliding slot having a proximal end extending to the intermediary thumbwheel and a distal end extending to a middle of the intermediary slide, and an intermediary fastener is fixedly connected to the third slide button, wherein the intermediary fastener is slidably fitted with the intermediary sliding slot.

16. The handle mechanism according to claim 1, wherein the body comprises a first sleeve, an intermediary sleeve, a second sleeve, and a junction section, wherein a distal end of the first sleeve, a distal end of the intermediary sleeve, and a distal end of the second sleeve are all connected to a proximal end of the junction section, and a distal end of the junction section is configured to be connected to a multi-lumen catheter; and the first anchor delivery device is assembled with the first sleeve, the second anchor delivery device is assembled with the second sleeve, the locking and cutting device is assembled with the intermediary sleeve, and the tightening device is assembled with the junction section,
wherein the first anchor delivery device is configured to control the first tissue anchor by means of the multi-lumen catheter; the second anchor delivery device is configured to control the second tissue anchor by means of the multi-lumen catheter; the tightening device is configured to pull the suture member by means of the multi-lumen catheter; and the locking and cutting device is configured to lock the suture member to the inner tubular member, cut the suture member, and completely release the inner tubular member and a portion of the suture member connected to the inner tubular member, by means of the multi-lumen catheter.

17. The handle mechanism according to claim 16, wherein a distal end of the first anchor delivery device is movably disposed in the first sleeve, a distal end of the locking and cutting device is movably disposed in the intermediary sleeve, and a distal end of the second anchor delivery device is movably disposed in the second sleeve.

18. The handle mechanism according to claim 16, wherein a first axis of the first sleeve and a second axis of the second sleeve are distributed at an acute angle, and a third axis of the intermediary sleeve is located between the first axis and the second axis.

19. The handle mechanism according to claim 16, wherein the body further comprises a spring tube having a proximal end connected to a distal end of the junction section and a distal end configured to be coupled to the multi-lumen catheter.

20. The handle mechanism according to claim 16, wherein the tightening device comprises a rotary wheel, wherein the rotary wheel is rotatably connected to the body, and a proximal end of the suture member is wound around the rotary wheel; and the rotary wheel rotates about a shaft axis perpendicular to a third axis of the intermediary sleeve.

21. An operation method, which is implemented using the handle mechanism according to claim 1, comprising:
  accessing and visualizing a treatment area using an endoscope;
  delivering distal ends of the first tissue anchor, the second tissue anchor, the inner tubular member, and the suture member, to a distal end of the endoscope through a working channel of the endoscope;
  operating the first anchor delivery device to anchor the first tissue anchor into a first target tissue and release the first tissue anchor;
  operating the second anchor delivery device to anchor the second tissue anchor into a second target tissue and release the second tissue anchor;
  operating the tightening device to pull the suture member and tighten the first tissue anchor and the second tissue anchor connected to the suture member, so as to tighten the first target tissue and the second target tissue; and
  operating the locking and cutting device to lock the suture member to the inner tubular member, cut the suture member, and completely release the inner tubular member and a portion of the suture member connected to the inner tubular member.

* * * * *